United States Patent
Liao et al.

(10) Patent No.: US 6,566,081 B1
(45) Date of Patent: May 20, 2003

(54) METHODS OF IDENTIFYING A COMPOUND WHICH MODULATES THE NON-TRANSCRIPTIONAL NON-MAP-KINASE INDUCED EFFECTS OF STEROID HORMONES

(75) Inventors: James K. Liao, Boston, MA (US); William Chin, Indianapolis, IN (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/680,695

(22) Filed: Oct. 6, 2000

Related U.S. Application Data

(60) Provisional application No. 60/158,173, filed on Oct. 7, 1999, provisional application No. 60/158,525, filed on Oct. 8, 1999, provisional application No. 60/163,964, filed on Nov. 8, 1999, and provisional application No. 60/163,953, filed on Nov. 8, 1999.

(51) Int. Cl.$^7$ .................... G01N 33/53; C12Q 1/68
(52) U.S. Cl. .................... 435/7.2; 435/6; 436/501
(58) Field of Search .................... 435/7.2, 6; 436/63, 436/501; 530/300

(56) References Cited

U.S. PATENT DOCUMENTS 5,688,810 A    11/1997    Jones et al.

FOREIGN PATENT DOCUMENTS

| | | |
|---|---|---|
| EP | 0635268 A1 | 1/1995 |
| EP | 0640339 A1 | 3/1995 |
| EP | 0658343 A1 | 6/1995 |
| EP | 1076091 A1 | 2/2001 |
| WO | 93/21328 | 10/1993 |
| WO | 96/01108 | 1/1996 |
| WO | 96/12024 | 4/1996 |
| WO | 96/21656 | 7/1996 |
| WO | 98/03634 | 1/1998 |
| WO | 98/10771 | 3/1998 |
| WO | 98/43647 | 10/1998 |
| WO | 98/50380 | 11/1998 |
| WO | 99/24471 | 5/1999 |
| WO | 99/45930 | 9/1999 |

OTHER PUBLICATIONS

Whitfield et al. Steroid hormone receptor: evolution, ligands and molecular basis of biological function. J. Cell. Biochem. Suppls. 32/33:110–122, 1999.*

Hall et al. The multifaceted mechanisms of estradiol and estrogen receptor signaling. J. Biol. Chem. 276:36869–36872,2001.*

Simoncini,, et al., "Activation of Estrogen Receptor–α Increases Endothelial Nitric Oxide Synthase Activity via the Phosphatidylinositol 3–Kinase–Akt Pathway", Circulation / Supplement, vol. 100, No. 18, p. I.337, Nov. 2, 1999.

Michell, et al., "The Akt kinase signals directly to endothelial nitric oxide synthase", Current Biology, vol. 9, No. 15, pp. 845–848, Jul. 29, 1999.

Ui, et al., "Wortmannin as a unique probe for an intracellular signalling protein, phosphoinositide 3–kinase", TIBS, vol. 20, No. 8, pp. 303–307, Aug. 1995.

Kennedy, et al., "The PI–kinase/Akt signaling pathway delivers an anti–apototic signal", Genes and Development, vol. 11, No. 6, pp. 701–713, 1997.

Dodge, et al., "17β–Hydroxywortmannin: A Potent Inhibitor of Bone Resorption And Phosphatidylinositol–3–Kinase", Bioorganic and Medicinal Chemistry Letters, vol. 5, No. 15, pp. 1713–1718, Aug. 3, 1995.

Marte, et al., "PKB/Akt: connecting phosphoinositide 3–kinase to cell survival and beyond", TIBS, vol. 22, No. 9, pp. 355–358, Sep. 1, 1997.

Haynes, et al., "Membrane Estrogen Receptor Engagement Activates Endothelial Nitric Oxide Sunthase via the PI3–Kinase–Akt Pathway in Human Endothelial Cells", Circulation Research, vol. 8, No. 7, pp. 677–682, Jul. 7, 2000.

Richards, et al., "Insulin–like Growth Factor–1 (IGF–1) Receptor–Insulin Receptor Substrate Complexes in the Uerus", The Journal of Biological Chemistry, vol. 273, No. 19, pp. 11962–11969, May 8, 1998.

Pagazzi, et al., Nitric Oxide Inhibits Thrombin Receptor–activitating Peptide–induced Phosphoinositide 3–Kinase Activity in Human Platelets, The Journal of Biological Chemistry, vol. 274, No. 20, pp. 14368–14375, May 14, 1999.

Friedman, Zeev, Y. "The Antitumor Agent Tamoxifen Inhibits Breakdown of Polyphosphoinositides in GH4C1 Cells, The Journal of Pharmacology and Experimental Therapeutics", vol. 271, No. 1, pp. 238–245, Jun. 4, 1994.

Kalipada, et al., "Inhibition of Phosphatidylinositol 3–Kinase Induces Nitric–oxide Synthase in Lipopolysaccharide–or Cytokine–stimulated C6 Glial Cells", JBC, vol. 274, No. 11, pp. 7528–7536, Mar. 12, 1999.

Krasil'nikov, et al., "The role of phosphatidylinositol 3–kinase in the regulation of cell response to steroid hormones", Biochemica Et Biophysica Acte, vol. 1450, No. 3, pp. 434–443, Jul. 8, 1999.

Moss, et al., "Non–Transcriptional Actions OF The Steroid Hormone Estrogen: Sites and Mechanisms of Action", Society for Neuroscience Abstracts, vol. 23, No. 1–2, p. 838, 1997—Abstract.

Ahmad, et al., "Role of AKT1 in 17 beta–Etradiol–and Insulin–Like Growth Factor I (IGF–1) Dependent Proliferation and Prevention of Apoptosis in MCF–7 Breast Carcinoma Cells", Biochemical Pharmacology, vol. 58, No. 3, pp. 425–430, 1999—Abstract.

\* cited by examiner

Primary Examiner—Elizabeth Kemmerer
Assistant Examiner—Ruixiang Li
(74) Attorney, Agent, or Firm—Wolf, Greenfield & Sacks, P.C.

(57) ABSTRACT

This invention provides new methods and compounds for controlling the intracellular and physiological effects of steroid hormones, including but not limited to estrogen, through modulation of the interaction of such hormone receptors with phosphatidylinositol-3 kinase. Compounds and methods for controlling the activation of endotbelial nitric oxide synthase are also disclosed.

6 Claims, 14 Drawing Sheets

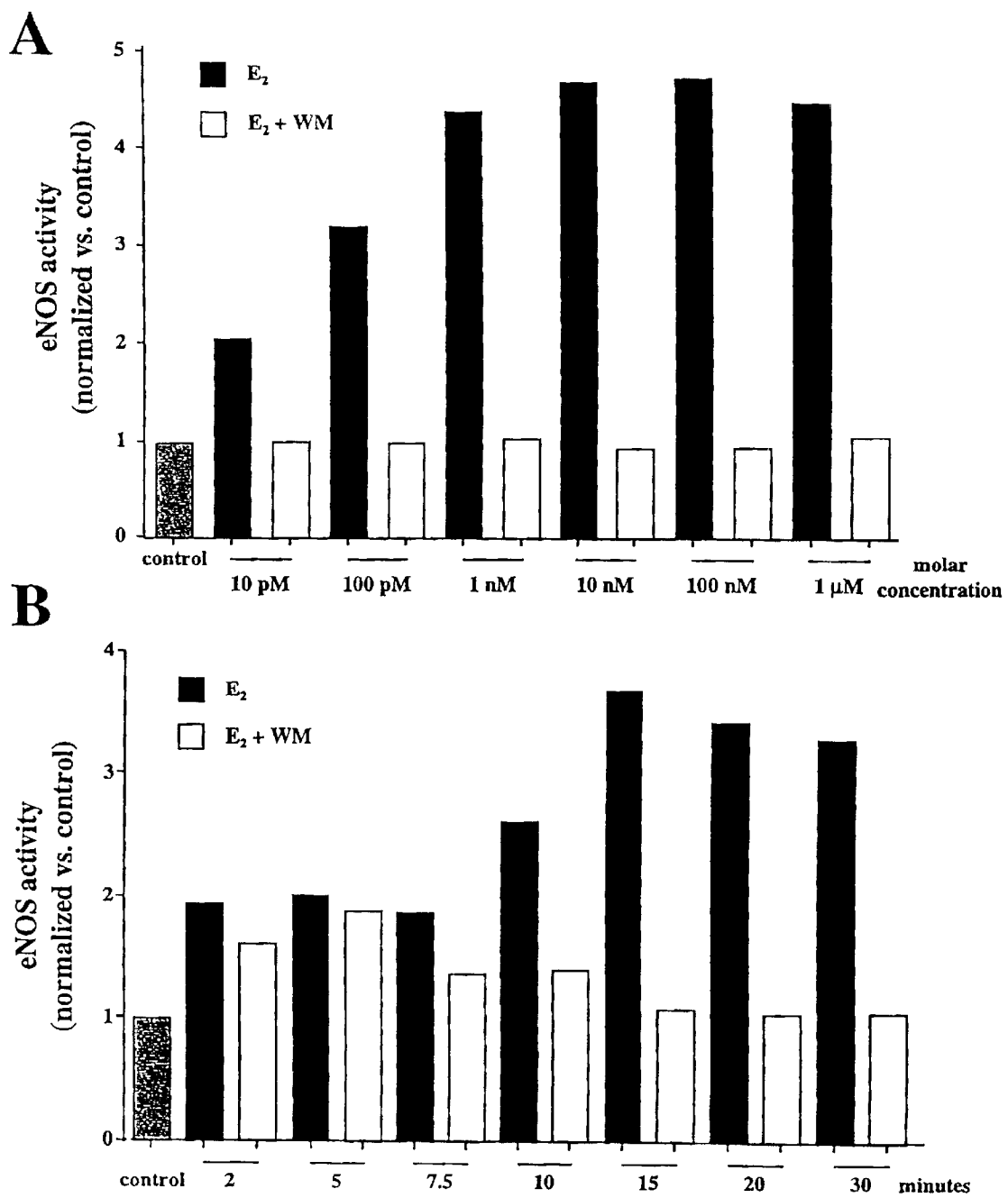
Figure 1A-B

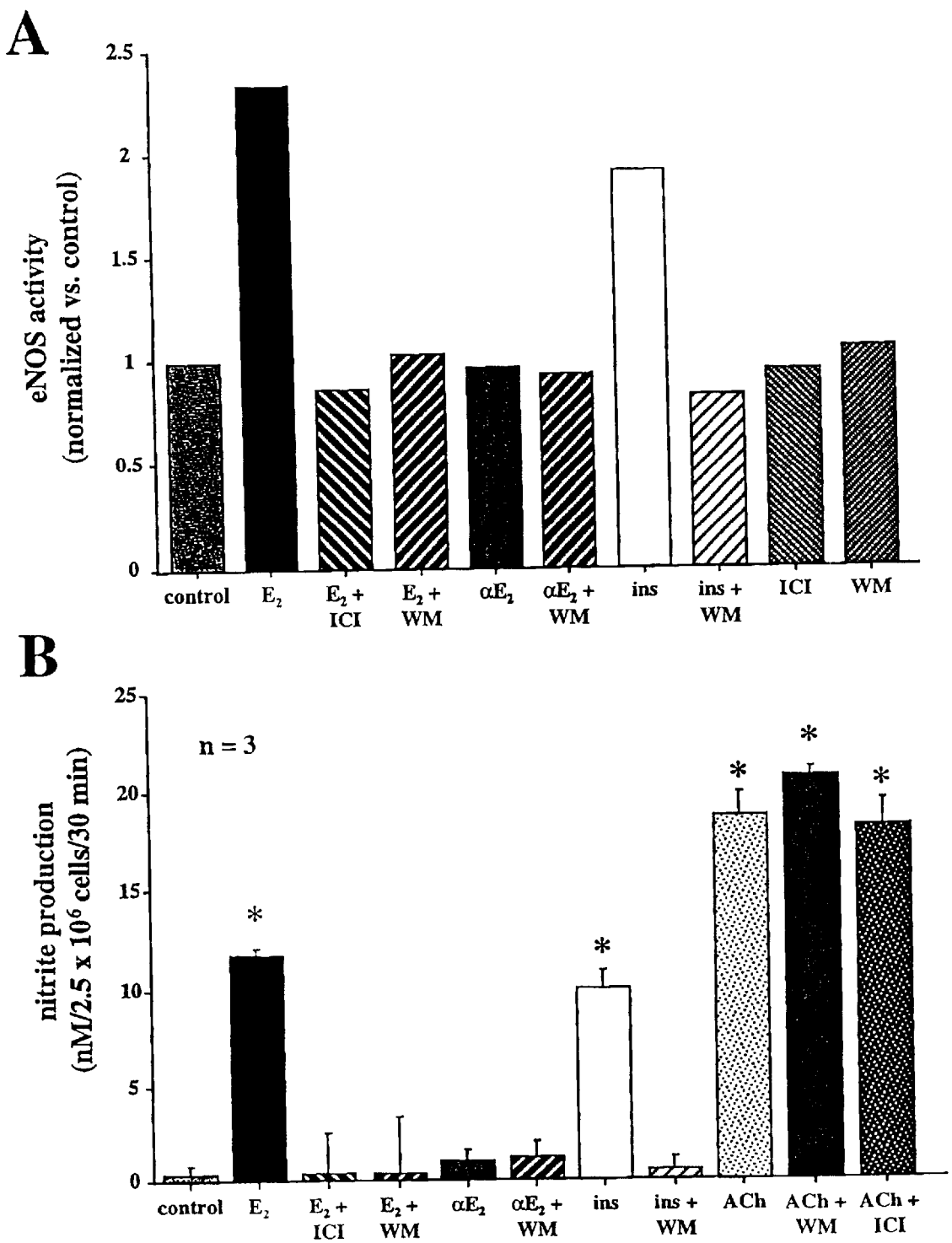
Figure 2A-B

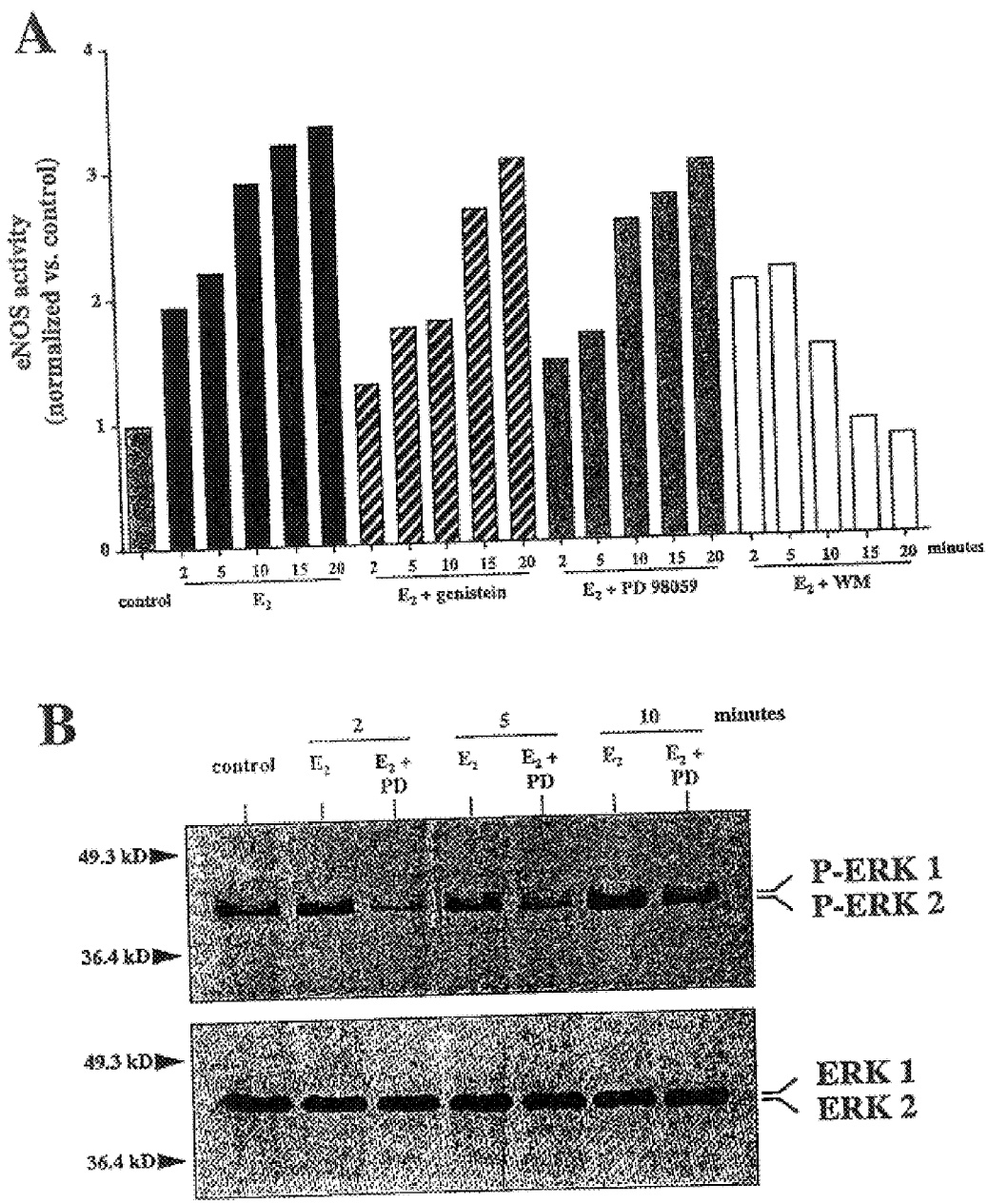
Figure 3A-B

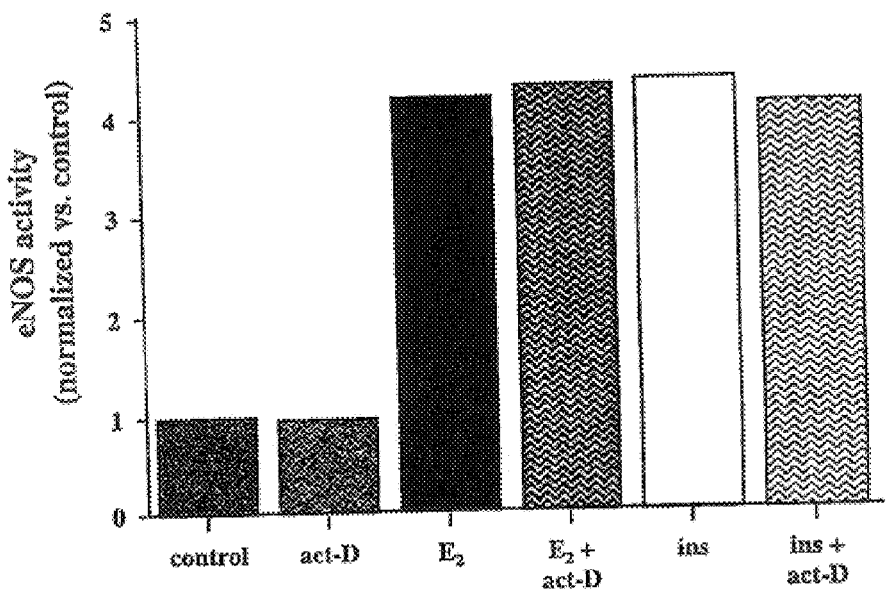
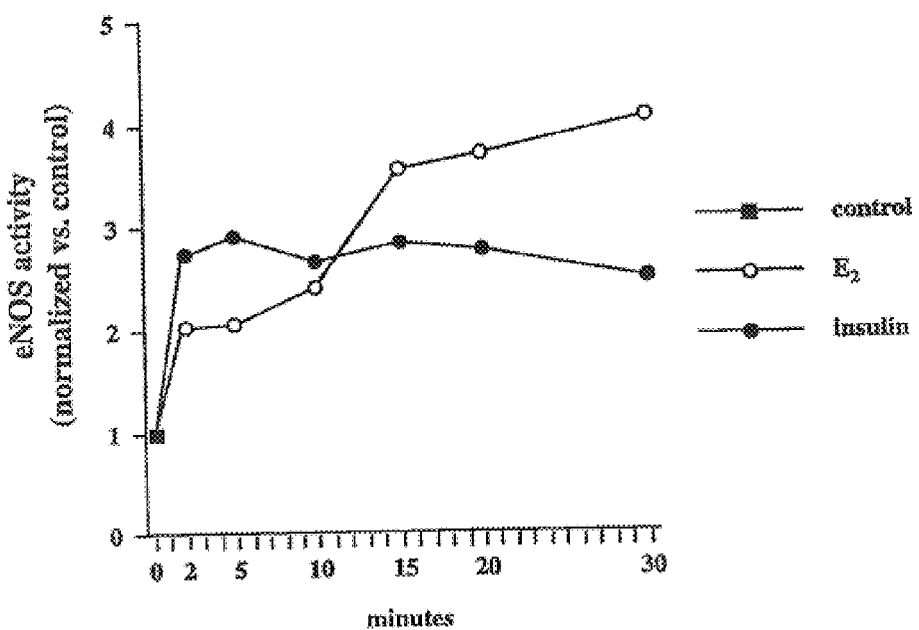
Figure 4A-B

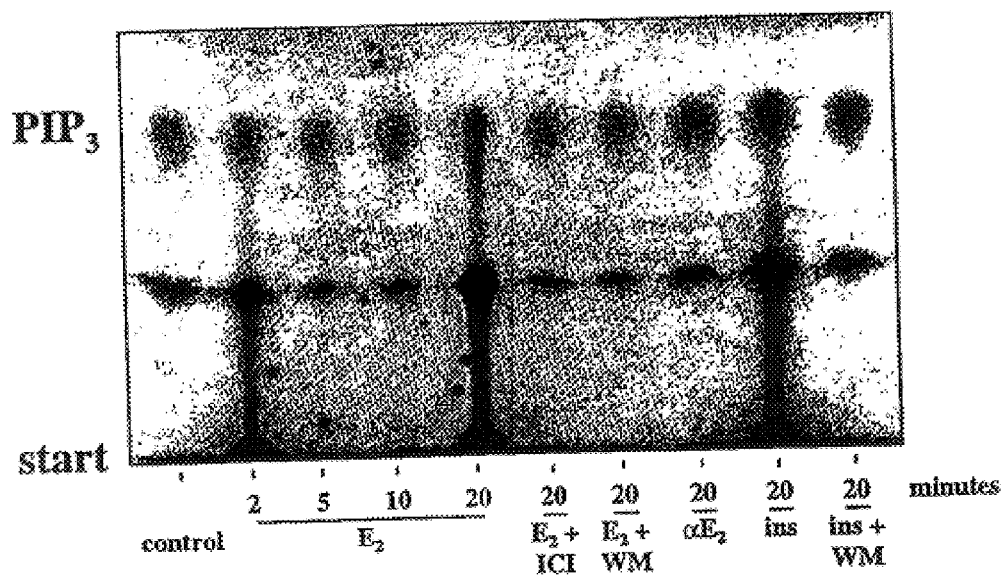
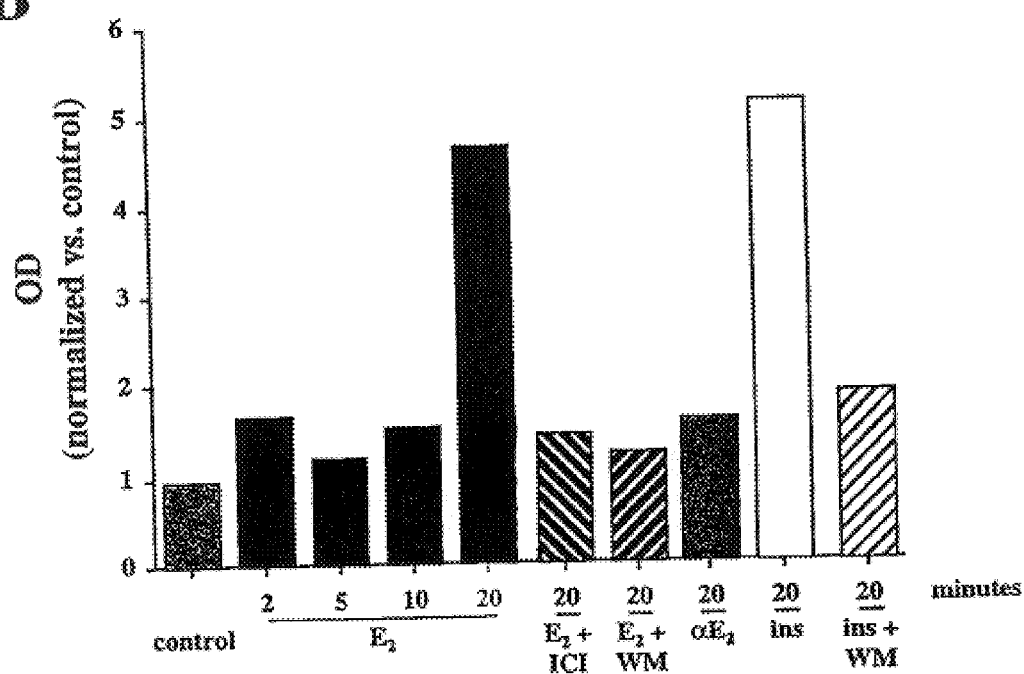
Figure 5A-B

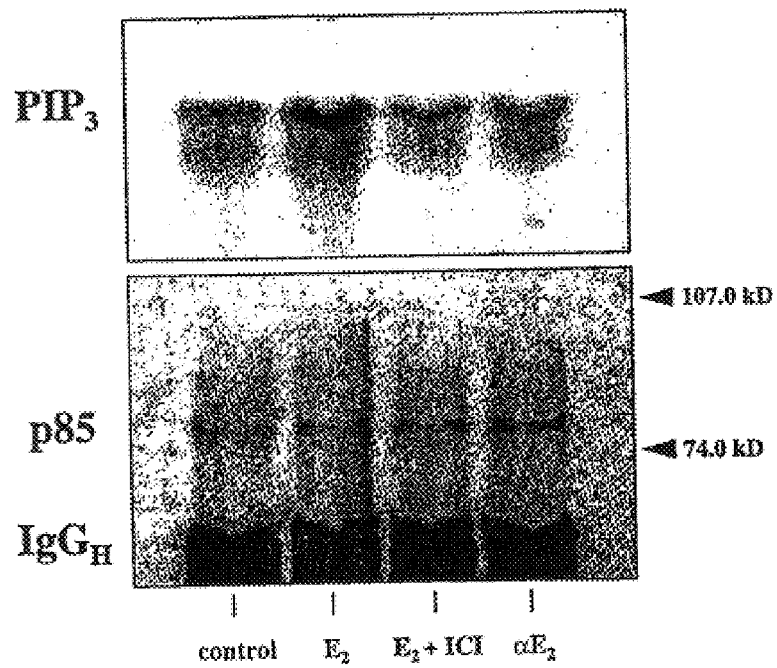
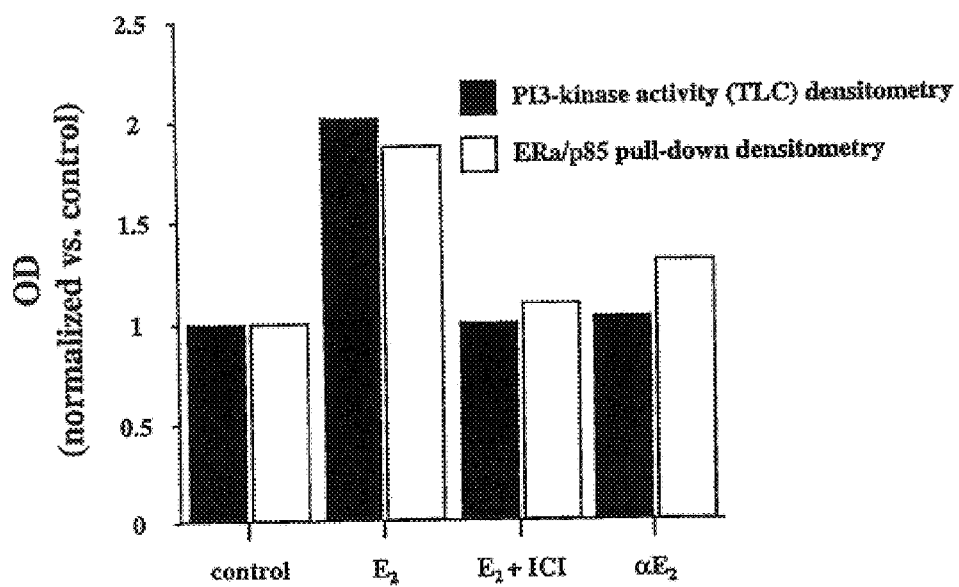
Figure 6A-B

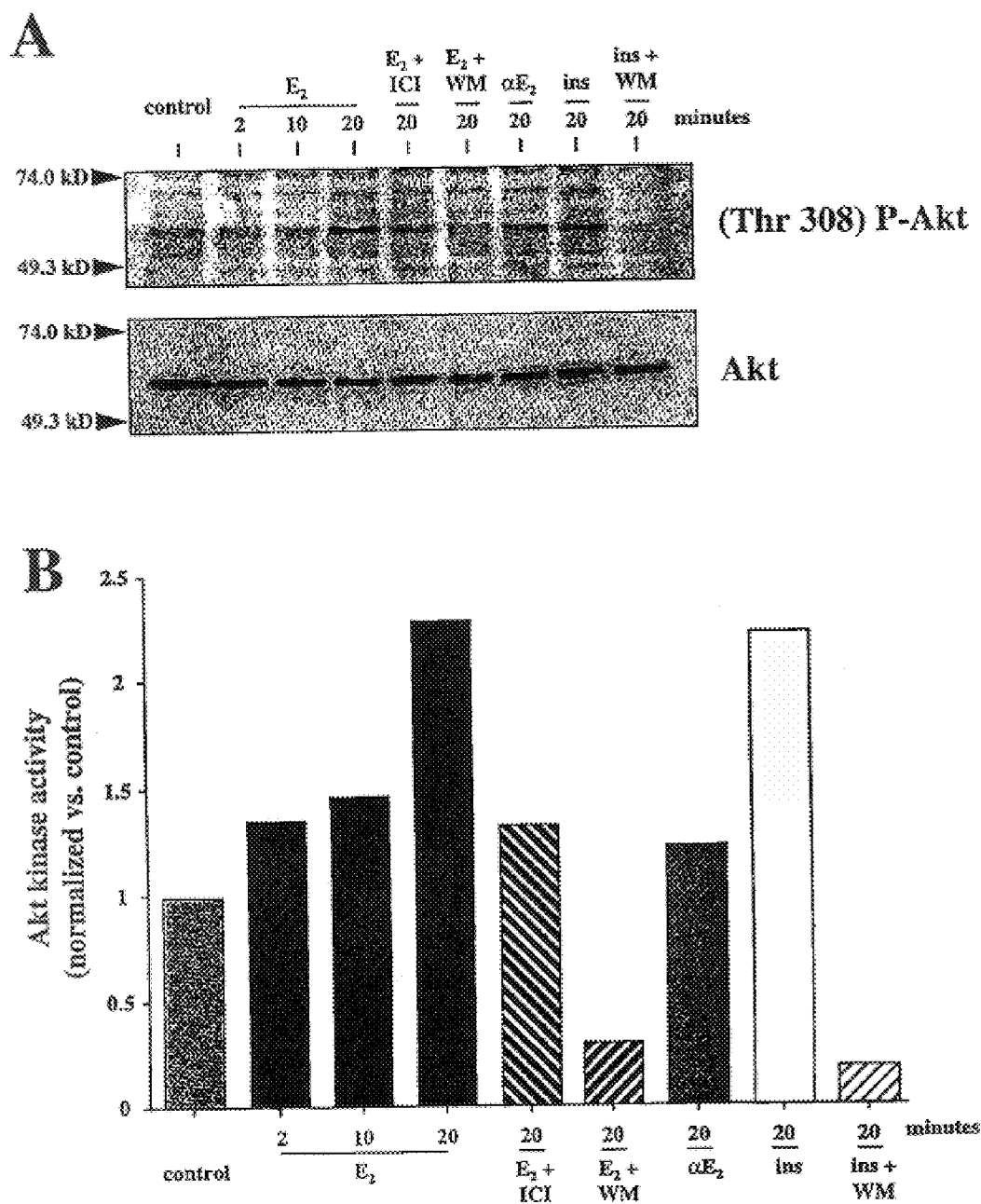
Figure 7A-B

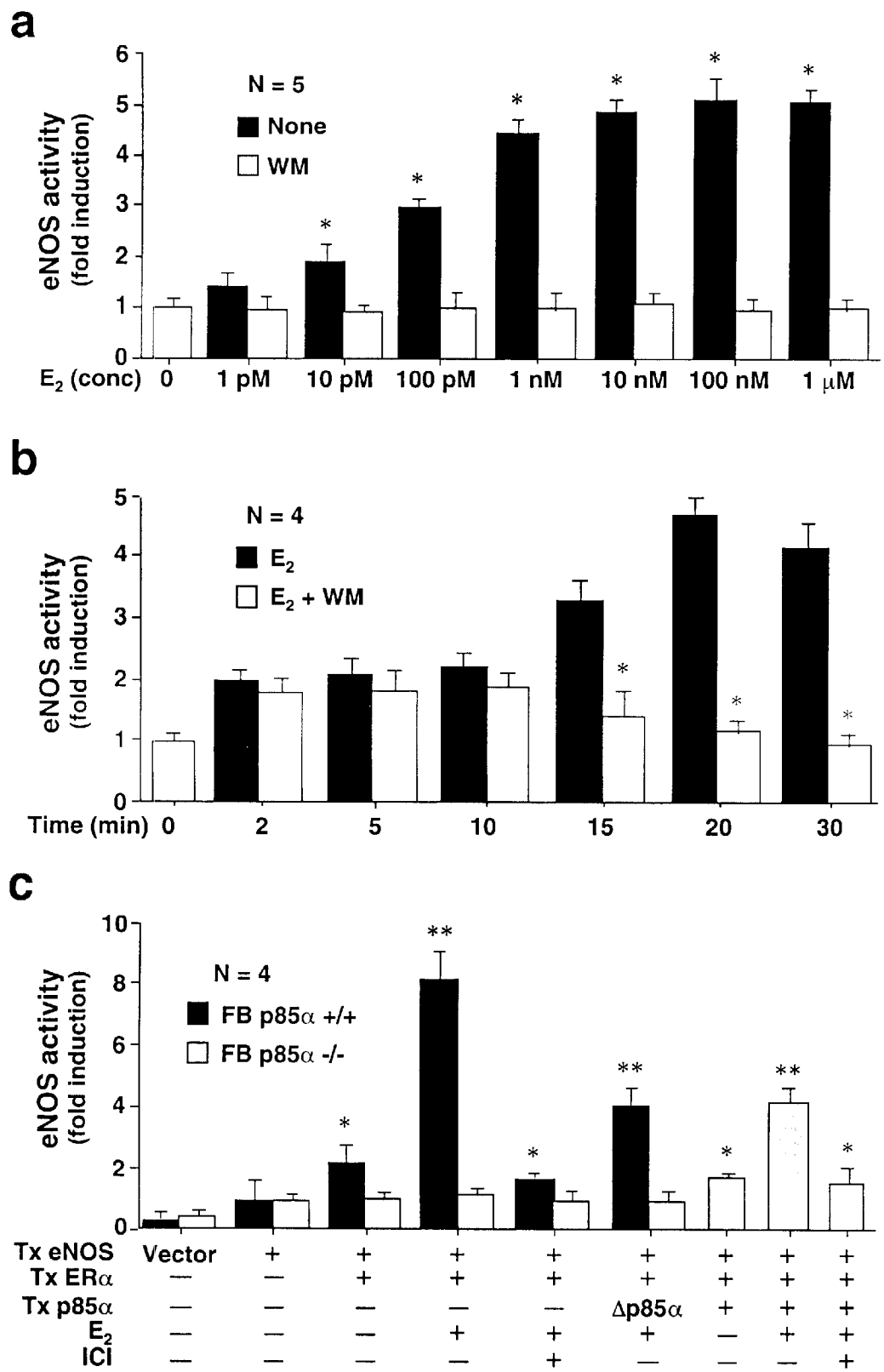
Figure 8 a-c

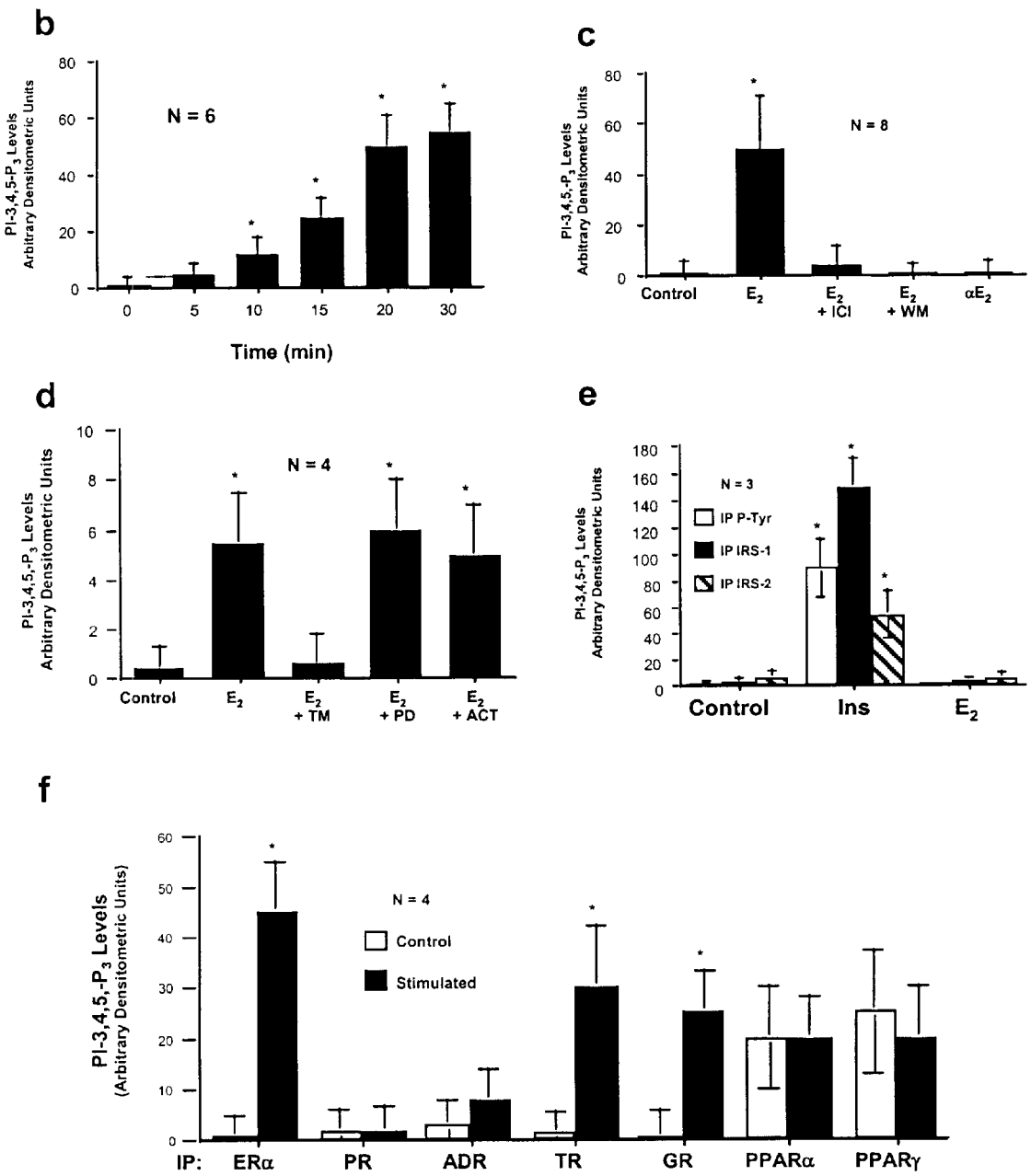
Figure 9 (cont) b-f

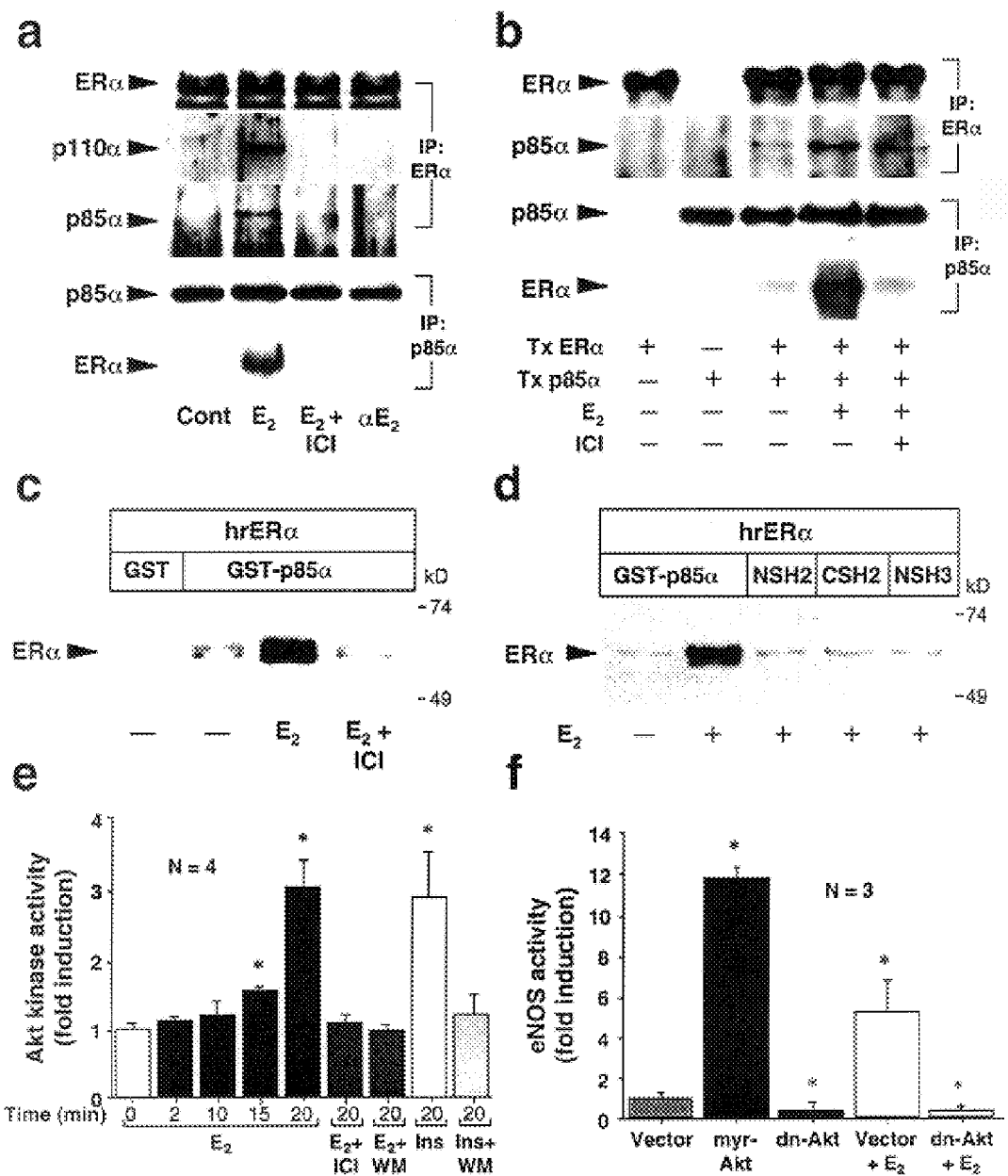
Figure 10 a-f

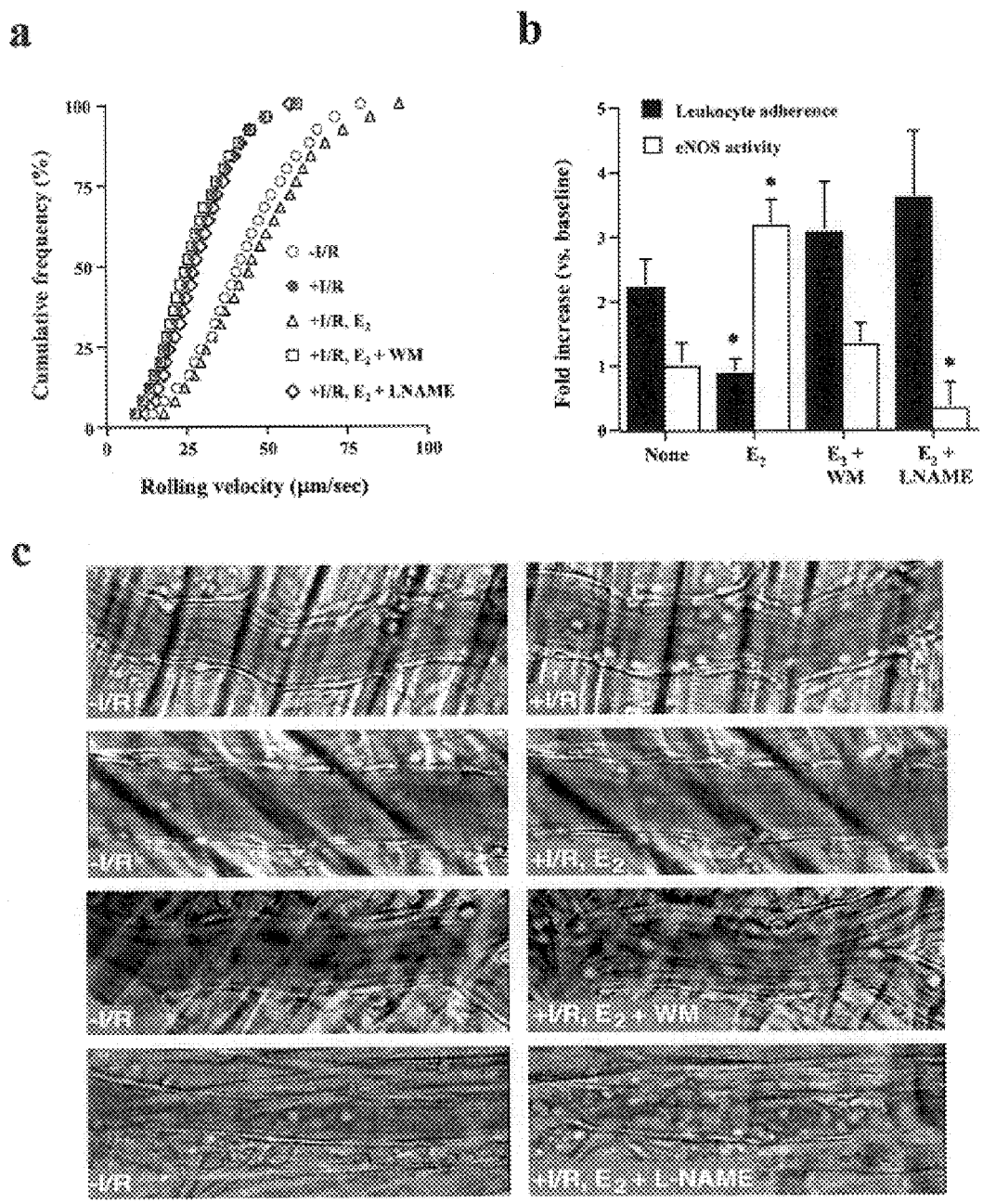
Figure 11 a-c

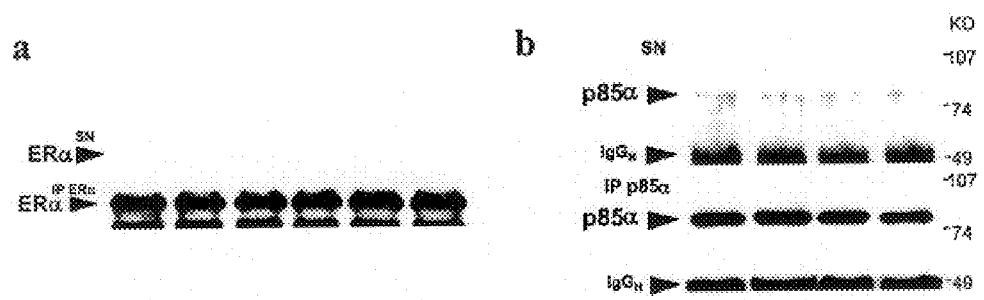
Figure 12a-b
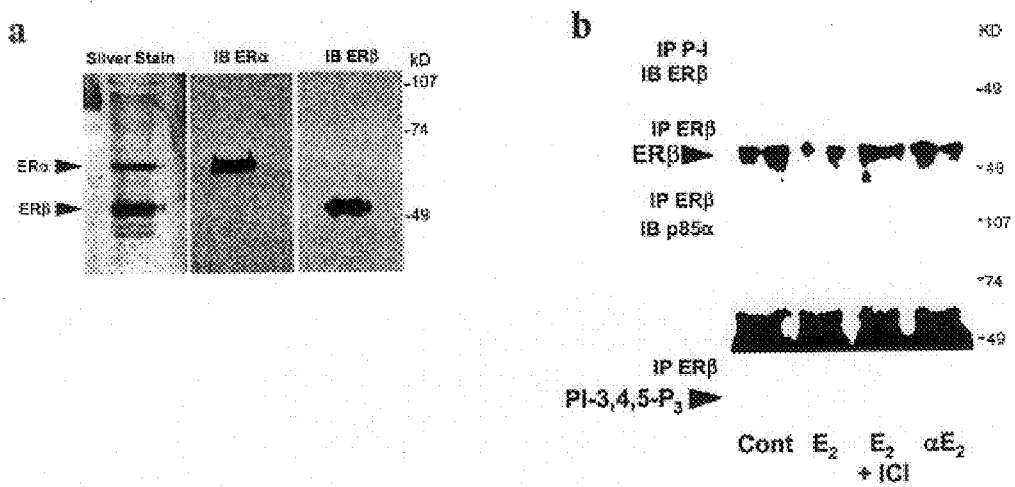
Figure 13a-b

METHODS OF IDENTIFYING A COMPOUND WHICH MODULATES THE NON-TRANSCRIPTIONAL NON-MAP-KINASE INDUCED EFFECTS OF STEROID HORMONES

CROSS REFERENCE TO RELATED APPLICATIONS

This application claims the benefit under 35 U.S.C. 119(e) of provisional U.S. patent application Ser. Nos. 60/163,964, filed Nov. 8, 1999, 60/163,953, filed Nov. 8, 1999, 60/158,525, filed Oct. 8, 1999, and 60/158,173, filed on Oct. 7, 1999, the entire contents of which are incorporated herein by reference.

The work involved in producing this subject matter was supported in part by the National Institute of Health Grant HL-52233. The U.S. Government may have certain rights in this invention.

BACKGROUND OF THE INVENTION

Estrogens elicit endothelium-dependent relaxation, apparently through activation of endothelial nitric oxide synthase, but the precise signaling pathway by which estrogens stimulate endothelial nitric oxide synthase (eNOS) activity is unknown. Here it is shown that the estrogen receptor (ER)-α interacts directly with phosphatidylinositol (PI) 3-kinase and that estrogen-induced eNOS activity is mediated via a novel non-nuclear mechanism involving the activation of the PI3-kinase/Akt pathway. The role of this pathway in modulation of physiologic conditions mediated by the estrogen and other receptors is disclosed and claimed.

BACKGROUND OF THE INVENTION

Recent epidemiological studies suggest that the use of hormone replacement therapy (HRT) by postmenopausal women is associated with improved outcomes from cardiovascular events.[1-4] Although some of the effects of HRT are related to the beneficial changes in lipid profile[5], other hemostatic effects such as the reduction in serum fibrinogen and plasminogen activator-inhibitor (PAI)-1 concentrations may also play an important role.[2,6] Furthermore, there is increasing evidence suggesting that a major part of estrogen's protective actions is due to its direct effects on the vascular wall. However, despite extensive research over the past few years, little information is available regarding the molecular mechanisms by which estrogens exert their protective effects.

Estrogens elicit endothelium-dependent vasodilation in animals[7,8] and humans[9-13] through the release of endothelium-derived nitric oxide (NO).[14] Estrogen stimulates NO release by increasing the activity and expression of Type III endothelial NO synthase (eNOS).[15,16] Although the activation of eNOS activity by estrogen occurs rapidly and involves the estrogen receptor (ER)-α and the mitogen-activated protein (MAP) kinase pathway, the signaling mechanism has yet to be fully established.[17] Recent studies suggest that stimuli of NO release such as bradykinin and laminar shear stress increase eNOS activity via phosphorylation of eNOS protein.[18,19] In particular, the phosphorylation of eNOS in response to laminar shear stress occurs via the PI3-kinase/Akt pathway.[20,21] Interestingly, another activator of the PI3-kinase/Akt pathway, insulin, has also been shown to increase eNOS activity.[22,23]

The PI3-kinase is a critical mediator of the cellular effects of many growth factors, such as platelet-derived growth factor (PDGF)[26], insulin[22] as well as vascular endothelial growth factor (VEGF)[27]. The PI3-kinase is a heterodimeric phosphoinositide kinase composed of an 85 kD (p85) adapter/regulatory subunit and a 110 kD (p110) catalytic subunit.[24] The PI3-kinase catalyzes the synthesis of phosphatidylinositol 3,4-biphosphate ($PIP_2$) and phosphatidylinositol 3,4,5-triphosphate ($PIP_3$).[25] These lipid mediators act as second messengers which activate proteins containing specific $PIP_3$-binding or pleckstrin homology (PH) domains. For example, the increase in intracellular $PIP_3$ and $PIP_2$ leads to the activation of phosphatidyl-dependent protein kinases, such as phosphatidyl-dependent kinase (PDK)-1 and -2.[28,29] The PDKs, in turn, selectively phosphorylate two threonine and serine residues of another important serine-threonine kinase called protein kinase B (PKB) or Akt. The activation of Akt has recently been shown to mediate many of the downstream cellular effects of PI3-kinase.[30,31]

This invention disclosure reveals that estrogens increase eNOS activity through the activation of the PI3-kinase/Akt pathway. Accordingly, this invention comprehends methods wherein the molecular signaling pathway by which estrogens activate eNOS is modulated, including interactions of ER-α with PI3-kinase.

SUMMARY OF THE INVENTION

Human endothelial cells were stimulated with estrogens and subsequent changes in PI3-kinase and eNOS activity were measured. The 17β-, but not 17α-, estradiol ($E_2$) increased PI3-kinase and eNOS activity in a time-dependent manner with maximum effect occurring 15–20 min after stimulation. The maximal effects of $E_2$ were completely blocked by the estrogen receptor antagonist, ICI 182,780, and a selective PI3-kinase inhibitor, wortmannin, but were only minimally affected by the mitogen-activating protein (MAP) kinase inhibitor, PD98059, or by the tyrosine kinase inhibitor, genistein. Co-immunoprecipitation studies demonstrated that the regulatory subunit of PI3-kinase, p85α, associates with the estrogen receptor (ER)-α, and that stimulation with $E_2$ increased both the amount and activity of co-immunoprecipitated PI3-kinase. The increase in PI3-kinase activity by $E_2$ corresponded temporally to the threonine phosphorylation of Akt and increase in eNOS activity.

Accordingly, this invention disclosure shows that the PI3-kinase/Akt signaling pathway mediates estrogen-induced activation of eNOS. Although the estrogen receptor is generally thought to function at the nuclear level, the present invention reveals that the activation of eNOS involves the direct association of ER-α with PI3-kinase p85α. These findings define a novel estrogen receptor signaling pathway in vascular endothelial cells and therapeutic strategies for treating vascular and non-vascular disorders.

Thus, it is one object of this invention to provide methods and compounds useful in modulating the level of activation of endothelial nitric oxide synthase.

Another object of this invention is to provide methods and compounds for modifying the effect of estrogen and related hormones on the level of PI3-kinase activity and the level of Akt activation.

Another object of this invention is to provide methods and compounds for modifying the interaction between the estrogen receptor, and related receptors, and the PI3-kinase.

Further objects and advantages of this invention will become apparent from a review of the complete disclosure and the claims appended to this invention disclosure.

BRIEF DESCRIPTION OF THE DRAWINGS

FIG. 1. 17β-estradiol activation of eNOS activity is blocked by wortmannin. A) Treatment of HSVEC with 10 nM 17β-estradiol (E$_2$) for 30 minutes increases eNOS activity measured as conversion of [$^3$H]L-arginine to [$^3$H] L-citrulline, vs. sham-treated cells (control), and this increase is blocked by performing the treatment in the presence of the estrogen receptor antagonist ICI 182,780 (E$_2$+ICI, ICI 182,780 concentration: 10 μM), as well as in the presence of the selective PI3-kinase inhibitor wortmannin (E$_2$+WM, wortmannin concentration: 30 nM). The inactive E$_2$ stereoisomer 17α-estradiol (αE$_2$), at the same concentration as E$_2$, has no effect on eNOS activity, nor is influenced by the cotreatment with wortmannin (αE$_2$+WM). Insulin (ins), 100 nM for 30 minutes, activates eNOS activity and its action is abolished by wortmannin (ins+ WM). The treatment of HSVEC with ICI 182,780 (ICI) or wormannin (WM) alone did not produce any effect on eNOS activity. Values are plotted as the fold induction of eNOS activity vs. sham-treated cells value, that is taken as 1. B) 17β-estradiol (E$_2$) 10 nM for 30 minutes increases NO release measured as nitrite accumulation, vs. sham-trated cells (control). ICI 182,780 (E$_2$+ICI, ICI 187,780 concentration: 10 μM) and wortmannin (E$_2$+WM, wortmannin concentration: 30 nM) both prevent E$_2$-induced NO release. 17α-estradiol (αE$_2$), 10 nM for 30 minutes, has a very low effect on nitrite accumulation, and is not influenced by the cotreatment with wortmannin (αE$_2$+WM). Insulin (ins), 100 nM for 30 minutes, activates nitrite release and its action is blocked by wortmannin (ins+WM). HSVEC treatment with acetylcholine (ACh), 10 μM for 30 minutes stimulates NO release, and this action is not influenced by the addition of wormannin (Ach+WM) or ICI 187,780 (ACh+ICI).

Figure 9:
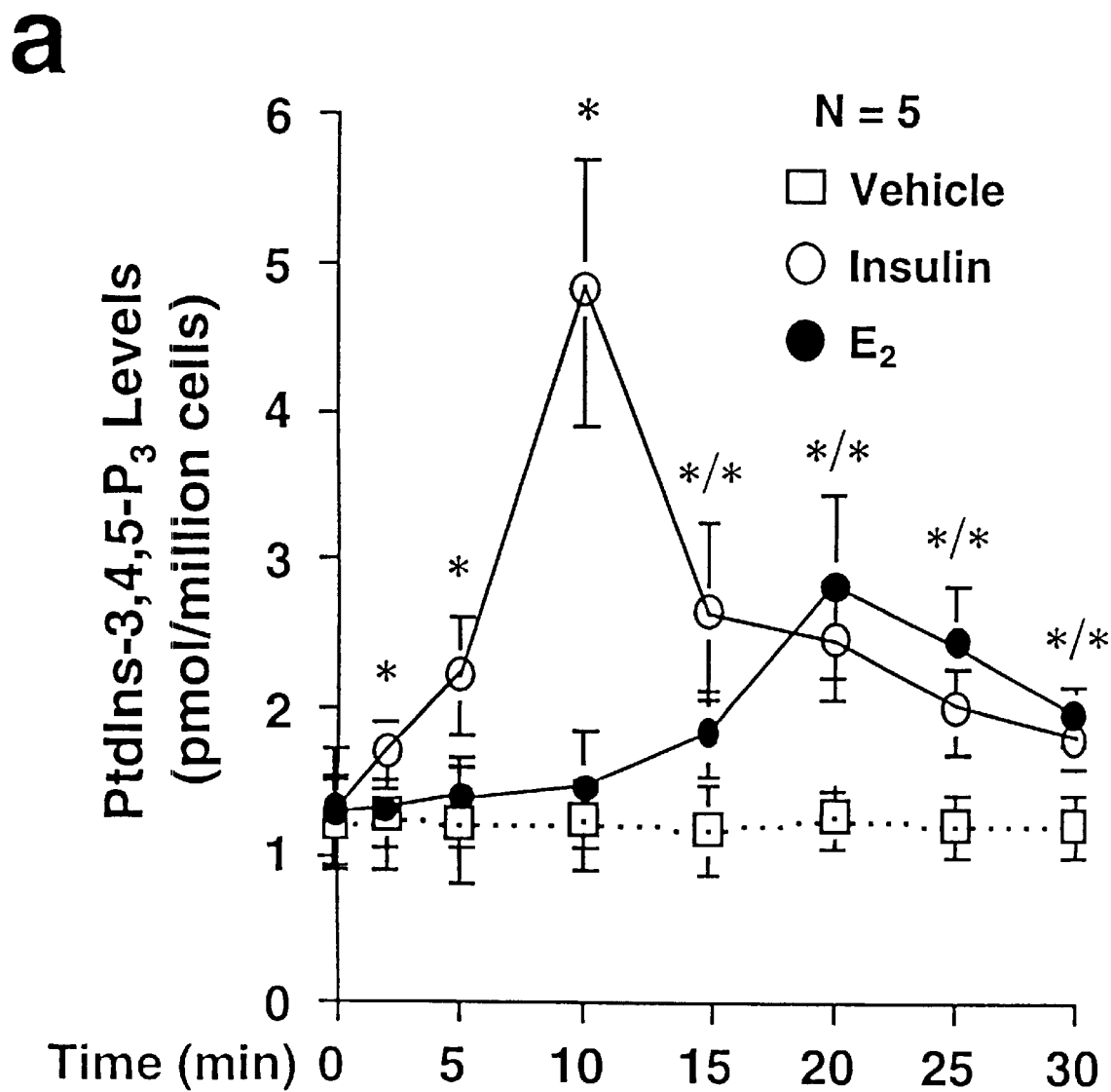

FIG. 2. 17β-estradiol time- and concentration-dependent activation of eNOS. A) A fixed concentration (10 nM) of 17β-estradiol (E$_2$, black bars) alone or in the presence of 30 nM wortmannin (E$_2$+WM, white bars) was used to treat for different times cultured HSVEC, and the induced eNOS activity was measured in the cell lysates. E$_2$ treatment induces a biphasic increase in eNOS activity, stimulating a rapid increase from 2 to 7.5 minutes of treatment, and a second, stronger increase after 10 minutes. Only the second phase is wortmannin-sensitive. Values are plotted as the fold induction of eNOS activity vs. unstimulated cells value, that is taken as 1. B) Increasing concentrations of E$_2$ (E$_2$, black bars) alone or in the presence of 30 nM wortmannin (E$_2$+ WM, white bars) were used to treat HSVEC for 30 minutes. E$_2$ increases eNOS activity starting from 10 pM, and reaches a maximal effect at 10 nM. Wortmannin treatment blocks E$_2$ effect at all concentrations tested. Values are plotted as the fold induction of eNOS activity vs. unstimulated cells value, that is taken as 1.

FIG. 3. Relative role of MAP kinases, tyrosine kinases and PI3-kinase in 17β-estradiol-induced eNOS activation. A) HSVEC were treated for different times with 17β-estradiol (E$_2$) (10 nM) alone or in the presence of the tyrosine kinase inhibitor genistein (E$_2$+genistein) (50 μM), of the MAP kinase kinase (MEK) inhibitor PD 98059 (E$_2$+PD 98059) (5 μM), or of the PI3-kinase inhibitor wortmannin (E$_2$+WM) (30 nM). Genistein and PD 98059 both blunt E$_2$-induced eNOS activity, but their effect is limited to the first 5–10 minutes of stimulation, while they do not block the delayed, stronger activation of eNOS. Wortmannin instead is ineffective on the E$_2$-induced eNOS activity during the first 5 minutes, but completely abolishes the effect of E$_2$ that ensues from 10 minutes and on. Values are plotted as the fold induction of eNOS activity vs. sham-treated cells value, that is taken as 1. B) To verify the efficacy of the MEK inhibitor PD 98059 in our experimental conditions, HSVEC were treated for different times with either 10 nM E$_2$ alone (E$_2$) or with 10 nM E2 and 5 μM PD 98059 (E$_2$+PD), and cell lysates were immunoblotted for the differential detection of the non-phosphorylated (total cellular content) or phosphorylated (activated) form of the MEK targets, the MAP kinases ERK 1 and 2. In absence of significant variation of ERK 1/2 total protein content (lower panel), E$_2$ induced an increased phosphorylation of the two proteins, starting from 2 minutes of treatment (upper panel). PD 98059 in our experimental conditions abolished the increased phosphorylation at each time point tested, confirming the efficacy of the compound in the conditions used (upper panel).

FIG. 4. Possible role of membrane-associated estrogen receptors and differences between 17β-estradiol and insulin kinetics for eNOS activation. A) To clarify if E$_2$ acute activation of eNOS may be dependent on a classical nuclear, gene transcription-dependent mechanism, HSVEC were treated for 2 hours with 5 μg/mL of the specific RNA polymerase inhibitor actinomycin D before the addition of 10 nM E$_2$ (E$_2$) or insulin (ins, 100 nM) for 30 minutes. Both the compounds induced a marked increase of eNOS activity, and actinomycin D pretreatment did not affect the action of the two molecules nor had any effects by itself. Asterisks indicate a significant difference vs. control. B) To study if E$_2$ and insulin may activate eNOS through common pathways, a parallel time course was performed, treating HSVEC with 10 nM E$_2$ (black circles) or with 100 nM insulin (white circles). While E$_2$ produced a biphasic increase in eNOS activity, insulin action was immediately maximal, reaching a peak within 2 minutes, without significant further increases. Values are plotted as the fold induction of eNOS activity vs. sham-treated cells value (white square), that is taken as 1.

FIG. 5. 17β-estradiol activates PI3-kinase in human endothelial cells. HSVEC were either vehicle-treated (control) or treated with 10 nM E$_2$ alone (E$_2$) for different times. E$_2$-treatment induced a strong activation of PI3-kinase, measured as $^{32}$P-labelled phosphatydilinositol 3 phosphate (PI 3 P) by immunoprecipitated PI3-kinase, and this increase was evident only after 20 minutes of incubation with E$_2$. HSVEC treatment with 10 nM E$_2$ (for 20 minutes) in the presence of 10 μM ICI 187,780 (E$_2$+ICI) or of 30 nM wortmannin (E$_2$+WM) was associated with a full inhibition of E$_2$-induced PI3-kinase activation, and the treatment with 10 nM 17α-estradiol for 20 minutes (αE$_2$) was also ineffective. Insulin treatment (100 nM for 20 minutes, ins) also induced a marked activation of PI3-kinase, and its action was similarly blocked by 30 nM wortmannin (ins+WM). B) The bars in represent the corresponding intensities of the autoradiographic signals obtained from the experiment shown in FIG. 5A, as estimated by quantitative densitometric analysis.

FIG. 6. Estrogen receptor-a physically interacts and activates PI3-kinase A) HSVEC lysates either vehicle-treated (control) or treated with 10 nM E$_2$ alone (E$_2$) for 20 minutes were immunoprecipitated with an antibody vs. ER-α, and subsequently subjected to either Immunoblotting for the PI3-kinase regulatory subunit p85α (lower panel), or used for a PI3-kinase activity assay (upper panel). Control ER-α immunoprecipitates contained PI3-kinase activity, measured as $^{32}$P-labeled phosphatydilinositol 3 phosphates (PI 3 P), and E$_2$-treatment was associated with a strong activation of PI3-kinase (upper panel). This activation was mirrored by an increased physical association of p85α in ER-α immunoprecipitates vs. the control lysates (lower panel). HSVEC treatment with 10 nM E$_2$ (for 20 minutes) in the presence of 10 μM ICI 187,780 (E$_2$+ICI) was associated with a full inhibition of $E_2$-induced co-precipitated PI3-kinase activation, and the treatment with 10 nM 17α-estradiol for 20 minutes ($\alpha E_2$) was also ineffective (upper panel). Parallelely, ICI 187,780 treatment decreased also the association between ER-α and the p85α, and 17α-estradiol did not significantly enhanced the interaction between the two proteins (lower panel). B) The bars represent the corresponding intensities of the bands obtained from the experiment shown in FIG. 6A, as estimated by quantitative densitometric analysis.

FIG. 7. 17β-estradiol activates Akt/PKB in human endothelial cells. A) HSVEC were either vehicle-treated (control) or treated with 10 nM $E_2$ alone ($E_2$) for different times. $E_2$-treatment triggered a differential phosphorylation of the two regulatory residues of Akt/PKB in absence of variations of the total cellular content of Akt/PKB protein (lower panel). Thr 308 was phosphorylated after 20 minutes of treatment (upper panel), and the phosphorylation was blocked by the presence of either 10 μM ICI 187,780 ($E_2$+ICI) or of 30 nM wortmannin ($E_2$+WM), while Ser 473 underwent to a slight decrease in the phosphorylation status in the first 10 minutes of treatment with 10 nM $E_2$ alone ($E_2$), before being hyperphosphorylated after 20 minutes (middle panel). Anyway, $E_2$-induced Ser 473 phosphorylation was not inhibited by ICI 187,780 (10 μM, $E_2$+ICI) but only by wortmannin (30 nM, $E_2$+WM). The treatment with 10 nM 17α-estradiol for 20 minutes ($\alpha E_2$) was ineffective on both the residues. Insulin treatment (100 nM for 20 minutes, ins) also induced a similar phosphorylation of the two residues, and its action was blocked by 30 nM wortmannin (ins+WM). B) $E_2$ (10 nM, $E_2$) activated Akt/PKB kinase activity, measured as phosphorylation of a peptide corresponding to the phosphorylation site of glycogen synthase kinase-3, specifically targeted by Akt/PKB by immunoprecipitated Akt/PKB kinase, and the increase was triggered only after 20 minutes of incubation with $E_2$. HSVEC treatment with 10 nM $E_2$ (for 20 minutes) in the presence of 10 μM ICI 187,780 ($E_2$+ICI) nearly completely abolished $E_2$-induced Akt kinase activity, and the addition of 30 nM wortmannin ($E_2$+WM) was associated with a full inhibition of $E_2$-induced PI3-kinase activation. The treatment with 10 nM 17α-estradiol for 20 minutes ($\alpha E_2$) was ineffective. Insulin treatment (100 nM for 20 minutes, ins) induced a marked activation of Akt/PKB kinase activity, and its action was prevented by 30 nM wortmannin (ins+WM).

FIG. 8. Activation of eNOS by estrogen is mediated by PI3K. a, Concentration- and b, time-dependent effects of $E_2$ and wortmannin (WM, 30 nM) on eNOS activity (fold induction vs. baseline) in human vascular endothelial cells. *indicates $p<0.05$ compared to unstimulated or $E_2$ stimulation. c, $E_2$-stimulated NOS activity in murine p85α+/+ and p85α−/− fibroblasts (FB) transfected (Tx) with vector (pcDNA3), eNOS, ERα, p85α, or dominant-negative p85α (Δp85α) cDNAs. *indicates $p<0.05$ compared to transfection with eNOS cDNA alone and **indicates $p<0.05$ compared to transfection with ERα and eNOS cDNAs.

FIG. 9. Estrogen stimulates ERα-associated PI3K activity. a, Effect of vehicle (ethanol 0.01% v/v), $E_2$(10 nM) or insulin (Ins, 100 nM) on endogenous PtdIns-3,4,5-$P_3$ levels. *indicates $p<0.05$ compared to vehicle. b, Time-dependent effect of $E_2$ on ERα, p85α, and PI3K activity ($PIP_3$) in ERα immunoprecipitate (IP). c, Effect of ICI (10 μM) or WM on $E_2$or 17α-estradiol ($\alpha E_2$)-stimulated ERα-associated PI3K activity. Cells were pre-treated with ICI or WM for 30 minutes. d, Effect of tamoxifen (TM, 1 μM), PD 98059 (PD, 5 μM) and actinomycin D (ACT, 5 μM) on ERα-associated PI3K activity. Inhibitors were added 2 h before $E_2$ stimulation. e, Effect of $E_2$ or Ins on p-Tyr- and IRS-1-associated PI3K activity. f, Effect of $E_2$, progesterone (Prog, 10 nM), testosterone (Test, 10 nM), thyroid hormone (Thyr, 10 nM), dexamethasone (Dex, 1 μM), WY14643 (WY, 100 μM), and 15-deoxy-$^{12,14}$-prostaglandin $J_2$ ($PGJ_2$, 100 μM) on PI3K activity in the corresponding steroid hormone nuclear receptor IPs.

FIG. 10. Ligand-dependent interaction of ERα with p85α. Effect of $E_2$ on ERα-p85α co-IP in a, non-transfected human endothelial cells and in b, murine p85α−/− fibroblasts transfected (Tx) with ERα, p85α, alone or in combination. c, Affinity purification using agarose-conjugated GST, GST-p85α, or d, GST-p85α N-terminal SH2 domain (NSH2, amino acids 321–470), C-terminal SH2 domain (CSH2, amino acids 576–724), or SH3 domain (NSH3, amino acids 1–80) fusion protein and human recombinant (hr) ERα. e, $E_2$- or Ins-stimulated Akt kinase activity. *indicates $p<0.05$ compared to no stimulation. f, Effect of $E_2$ on eNOS activity (fold induction over baseline) in endothelial cells transfected with adenovirus containing no Akt (vector), constitutively-active (myr), or a dominant-negative (dn) Akt. *indicates $p<0.05$ compared to vector alone.

FIG. 11. PI3K and NO mediate the vascular protective effects of estrogen. The number of leukocytes (cumulative frequency) with rolling velocities before (−) and after (+) ischemia and reperfusion (I/R). Effect of superfused WM (100 nM) or L-nitroarginine methylester (LNAME, 0.1 mM) on a, leukocyte rolling velocity, b, leukocyte adhesion, and eNOS activity in the murine cremaster muscle. Data are expressed as fold increase over baseline before I/R in the same paired venules. *indicates $p<0.001$ compared to untreated after I/R (None). c, Representative video images showing the same venules before (−) and after (+) I/R with the indicated treatments. White bar, 40 μM.

FIG. 12. Efficiency of immunoprecipitation using ERα and p85α antibody. a. Immunoblot of ERα in ERα immunoprecipitate (IP) and "left-over" supernatant (SN). b. Immunoblot of p85α in p85α immunoprecipitate (IP) and "left-over" supernatant (SN). This is representative of 5 separate experiments. Note that >95% of ERα and p85α were immunoprecipitated under our experimental conditions.

FIG. 13. Specificity of ERα and ERβ antibodies. Recombinant ERα and ERβ proteins were loaded in the same lane of a SDS/PAGE and then transferred onto PVDF membranes for immunoblotting with anti-ERα or anti-Eβ antibody. A corresponding gel was silver-stained to confirm the presence of both proteins. Cell lysates from non-transfected endothelial cells stimulated with $E_2$ (10 nM) or $\alpha E_2$ (10 nM), with and without ICI (10 μM), were immunoprecipitated (IP) with pre-immune (P-I) serum or anti-ERβ, and then immunoblotted with anti-ERβ or anti-p85α antibody as indicated. The ERβ IP was also assayed for PI3K activity. All experiments were repeated three to four times and yielded similar results. Note that ERβ does not interact with p85α.

Figure 14:
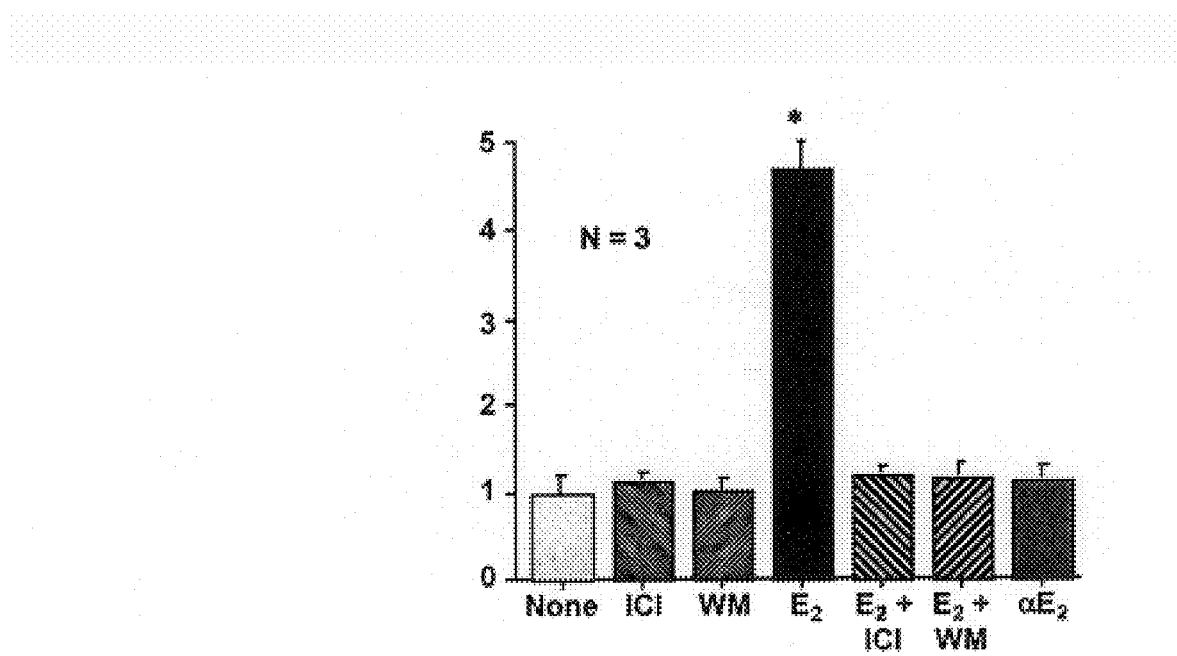

FIG. 14. Effect of $E_2$ (10 nM) and 17α-estradiol ($\alpha E_2$, 10 nM) on eNOS activity (fold induction over baseline) in the presence and absence of ER antagonist, ICI 187,780 (ICI, 10 μM) or wortmannin (WM, 30 nM). *indicates $p<0.05$ compared to unstimulated (None).

Figure 15:
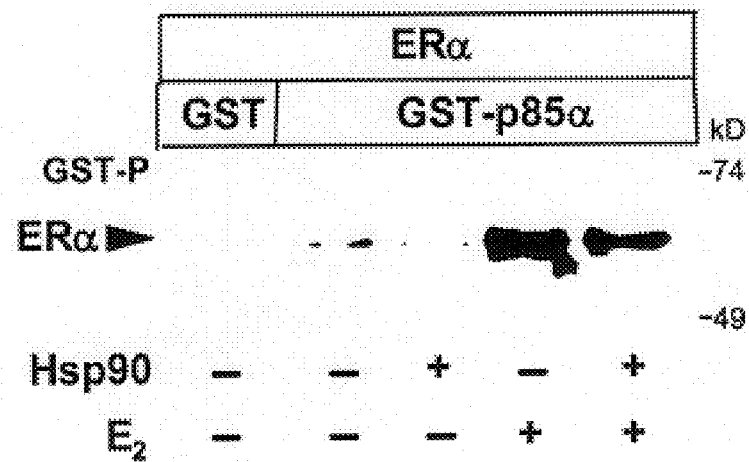

FIG. 15. Hsp90 inhibits ERα-p85α interaction. Recombinant ERα protein was added to agarose-conjugated GST or GST-p85α in the presence and absence of $E_2$ (10 nM) or heat shock protein 90 (Hsp90, 0.5 μg). The GST precipitate (GST-P) was immunoblotted with an anti-ERα antibody as indicated. Studies were performed 3 times with similar results.

DETAILED DISCLOSURE OF THE PREFERRED EMBODIMENTS OF THE INVENTION

In this invention disclosure, a novel signaling- mechanism by which estrogen increases eNOS activity via the PI3-kinase/Akt pathway is revealed. Surprisingly, this disclosure demonstrates that that the estrogen receptor, ER-α, can directly interact with the regulatory subunit of PI3-kinase via a non-nuclear mechanism. As shown herein, not only did p85 co-immunoprecipitate with ER-α, but also, the immunoprecipitate contain PI3-kinase activity. Furthermore, activation of PI3-kinase by estrogen leads temporally to the phosphorylation of Akt, the activation of Akt, and stimulation of eNOS activity. The activation of eNOS results from a specific interaction with the estrogen receptor as demonstrated by the complete blockade with the pure estrogen receptor antagonist ICI 187,780, as well as by the inability of the chemically-inactive estrogen stereoisomer, 17α-estradiol, to stimulate PI3-kinase and eNOS activity. Furthermore, all of these effects occur at physiologically relevant concentrations of the natural estrogen, 17β-estradiol. These findings, therefore, suggest an important physiological role of PI3-kinase in cellular processes mediated by estrogens. Indeed, the regulation of eNOS activity by estrogens may contribute to some of the vascular protective effects of these hormones. Methods and compounds for modulating these effects, as well as the effects of other steroid hormones which act through a similar mechanism, constitutes one significant embodiment of this invention.

As noted herein, the activation of eNOS by $E_2$ occurs in a biphasic manner, initially producing a rapid activity within the first five minutes of treatment and a subsequent but more substantial increase in eNOS activity after 10 minutes. This time-delayed activation of eNOS which is wortmannin-sensitive is the more important quantitatively, indicating that the PI3-kinase-mediated pathway may represents the principal molecular mechanism for $E_2$ and other steroid hormone-stimulated eNOS activity. In this regard, a recent report suggested that the MAP kinase and the tyrosine kinase signaling pathways may also be involved in the eNOS activation by estrogens[17]. The results provided herein indicate that the initial increase in eNOS activity may be mediated by tyrosine/MAP kinase pathway since the MEK inhibitor, PD98059, and the tyrosine kinase inhibitor, genistein, were able to block the initial, but not the later phase of $E_2$-stimulated eNOS activity. These findings suggest a direct relationship between the estrogen/estrogen receptor and the PI3-kinase/Akt signaling pathways.

By linking the estrogen receptor to PI3-kinase, one may gain greater insights into the actions of estrogens since PI3-kinase is known to mediate various cellular functions. Indeed, this lipid kinase controls many metabolic functions in different tissues and cell types such as the cellular uptake of glucose, the regulation of the membrane translocation of the glucose transporter, GLUT4[38], the control of glycogen synthesis[39] and lipolytic process[40]. The PI3-kinase/Akt pathway has also been implicated in the regulation of growth factor-induced cell growth and proliferation[41], as well as of the cellular apoptotic processes[27, 42, 43]. The insulin-induced eNOS activity has also been shown to be wortmannin-sensitive[23], and the instant findings are in agreement with these results showing that eNOS activation by physiological concentrations of insulin is associated with the activation of both PI3-kinase and of Akt. The kinetics of eNOS activation by $E_2$ and insulin, however, is temporally quite different. Whereas insulin stimulates PI3-kinase and eNOS activity within 2 min of stimulation, $E_2$ stimulated PI3-kinase and eNOS activity occurs after 15 min. These findings suggest that the molecular pathways which link the estrogen and insulin receptor to the activation of PI3-kinase are probably different, or at least that they are recruited at different time points.

In addition to eNOS activation, the activation of Akt by $E_2$ may represent a mechanism for the regulation of cell growth by estrogens. Indeed, estrogens have been shown to increase the risks for breast and endometrial cancers and can serve as a survival factor for human endothelial cells, preventing cytokine-induced apoptosis through an undetermined mechanism[45]. The Akt serine-threonine kinase is known to block apoptosis via the phosphorylation of multiple targets, including the BCL-2 family member BAD[46] and the cell death pathway enzyme caspase-9[47]. The induction of phosphorylation of these targets by estrogen-induced Akt activation may potentially provide a molecular link between the PI3-kinase/Akt pathway and the anti-apoptotic effects of estrogens.

In summary, this disclosure constitutes a report of a novel interaction between the estrogen/estrogen receptor and the PI3-kinase/Akt pathways in human endothelial cells and shows that this interaction mediates the acute activation of eNOS.

EXAMPLES

Having generally described the invention, the following examples are provided to include detailed written disclosure to assist those skilled in the art in their understanding of the means by which this invention may be practiced. However, it will be appreciated by those skilled in the art that the scope of this invention is not limited to the specifics of these examples. Thus, for example, those skilled in the art will appreciate that the physiological effects of estrogen mediated through the PI3-kinase, Akt and eNOS, are expected to apply to any hormone or receptor related to the estrogen receptor. Accordingly, the detailed disclosure provided herein with respect to the estrogen receptor is anticipated to be applicable to steroid hormones and their receptors, in general. Accordingly, the scope of this invention is to be comprehended by the claims attached hereto and their equivalents.

Example 1

Materials and Methods

A. Cell Cultures

Human endothelial cells were harvested enzymatically with Type IA collagenase (1 mg/mL) as described[32], and maintained in phenol red-free Medium 199 (Gibco BRL, Life Technologies, Gaithersburg, Md.), containing HEPES (25 mmol/L), heparin (50 U/mL), endothelial cell growth factor (ECGF) (50 µg/mL), L-glutamine (2 mmol/L), antibiotics, and 5% estrogen-deprived fetal bovine serum. Fetal bovine serum was deprived of estrogen by charcoal-stripping. Once grown to confluence the cells were replated on 1.5% gelatin-coated flasks at 20000 cells/cm². HSVEC isolated by this technique form a confluent monolayer of polygonal cells and express von Willebrand factor as determined by their content of immunoreactive protein. Cell number was assessed by direct cell counting of adherent cells, after trypsin detachment, in a Neubauer hemocytometer (VWR Scientifics). The percentage of cells excluding Trypan Blue after staining with the compound was taken as a measure of cell viability.

B. eNOS Activity Assay

Endothelial cells were grown to confluence on 55 cm² culture dishes, treated according to the indicated conditions, and harvested in ice-cold PBS containing 1 mM EDTA. The cell lysates were pelleted in a microfuge (2 minutes, 13000 rpm, 4° C.) and subsequently homogenized in a buffer containing 25 mM Tris-HCl, pH 7.4, 1 mM EDTA, 1 mM EGTA. eNOS activity was determined by measuring the conversion of [$^3$H]-arginine to [$^3$H]-citrulline. Rat cerebellum extracts, containing elevated amounts of neuronal NOS, were used as positive controls, while endothelial cell extracts incubated in the presence of the competitive eNOS inhibitor L-NAME (1 mM) served as negative controls.

C. Nitrite Assay

NO accumulation from serum-starved endothelial cells was determined by a modified nitrite assay using 2, 3 diaminonaphtalene as described previously.[33] Fluorescence of 1-(H)-naphtotriazole was measured with excitation and emission wavelengths of 365 and 450 nm, respectively. Standard curves were constructed with known amounts of sodium nitrite. Nonspecific fluorescence was determined in the presence of LNMA (3 mM).

D. PI3-kinase Assay

PI3kinase activity in endothelial cell lysates was assayed using the borate thin layer chromatography method, as described.[34] Following a 6 h incubation in serum- and estrogen-deficient medium 199, endothelial cells were treated according to the indicated conditions, washed, and harvested in ice-cold lysis buffer (137 mM NaCl, 20 mM Tris-HCl, pH 7.4, 1 mM CaCl$_2$, 1 mM Mg Cl$_2$, 0.1 mM Na$_3$VO$_4$, 1% NP-40). After pelleting the cell debris, the supernatant was incubated for 1 hour at 4° C. with 5 µL of a rabbit antiserum directed against the p85 regulatory subunit of the PI3-kinase (Upstate Biotechnology, Lake Placid, N.Y.), and immunoprecipitated with the addition of 50 µL of a 1:1 slurry of protein A-agarose for 1 hour at 4° C. Following centrifugation, the immunoprecipitates were washed three times with lysis buffer, three times with 0.1 M Tris-HCl, pH 7.4, 5 mM LiCl, 0.1 mM Na$_3$VO$_4$, followed by two washes with 10 mM Tris-HCl, pH 7.4, 150 mM NaCl, 5 mM EDTA, 0.1 mM Na$_3$VO$_4$.

The immunoprecipitates were then mixed with 50 µL Tris-HCl, pH 7.4, 150 mM NaCl, 5 mM EDTA, 20 µg of phosphatidylinositol (Sigma, Saint Louis, Mo.), 10 µL 100 mM MgCl$_2$ and 5 µL of a 0.88 mM ATP, 20 mM MgCl$_2$ solution, containing 30 µCi of [$\gamma$-$^{32}$P]ATP (3000 Ci/mmol; NEN Life Science Products, Boston, Mass.). The reaction was incubated at 37° C. for 10 minutes, and subsequently blocked by the addition of 20 µL of 6N HCl. The phospholipids were extracted with 160 µL of chloroform/methanol (1:1, v/v). 50 µL of the organic phase, containing the labeled PI3-kinase products were separated by borate thin layer chromatography on glass-backed Silica Gel 60 plates (EM Separations, Gibbstown, N.J.) pretreated with a solution containing 25 mM trans-1,2-diaminocyclohexane-N,N, N'N'-tetraacetic acid (CDTA, Sigma, Saint Louis, Mo.), 66% (v/v) ethanol and 0.06 N NaOH, dried for 1 hour and then baked at 100° C. for 15 minutes. The chromatography was developed with a solution containing 37.5% (v/v) methanol, 30% (v/v) chloroform, 22.5% (v/v) pyridine (Sigma, Saint Louis, Mo.), 1.33% (v/v) formic acid, 1 M boric acid and 8.5 mM butylated hydroxytoluene (Sigma, Saint Louis, Mo.), briefly dried and exposed to autoradiography.

E. Immunoblotting

After the different treatments, serum-starved endothelial cells were rinsed once with ice-cold PBS before addition of the lysis buffer (100 mM Tris-HCl, pH 6.8, 4% SDS, 20% glycerol, 1 mM sodium orthovanadate, 1 mM NaF, and 1 mM phenylmethylsulfonylfluoride) to the dishes on an ice tray. The cell lysates were scraped, boiled, and centrifuged for 2 min at 13000 rpm. Total cell lysates (40 µg of protein) and low range molecular weight markers (BIO-RAD, Hercules, Calif.) were separated by SDS-polyacrylamide gel electrophoresis (12% running, 4% stacking), electrophoretically transferred to polyvinylidene fluoride membranes (Immobilon P, 0.45 µm pore size) and incubated overnight at 4° C. with blocking solution (5% skim milk in TBS—0.1% Tween 20). Affinity-purified rabbit antibodies (0.4 µg of IgG/ml) vs. Akt, (Ser 473) phospho-Akt or (Thr 308) phospho-Akt (New England BioLabs, Beverly, Mass.), Erk1/2, (Tyr 204) phospho-Erk-1/-2 (Calbiochem, San Diego, Calif.) were incubated with the membranes overnight at 4° C. in TBS—0.1% Tween 20 containing 5% BSA. The blots were washed three times with TBS—0.1% Tween 20 and then treated with donkey anti-rabbit antibody (1:4000 dilution) coupled to horseradish peroxidase. Immunodetection was accomplished using the enhanced chemoluminescence kit (ECL Kit, Amersham Corp.).

F. Akt Kinase Assay

Immunoprecipitated Akt kinase activity was assayed on endothelial cell lysates by using the Aktl/PKBα immunoprecipitation kinase assay kit (Upstate Biotechnology, Lake Placid, N.Y.). Endothelial cells were starved in phenol red-free199 medium with 0.4% estrogen-deprived FBS, treated, washed, and then harvested in ice-cold Buffer A (50 mM Tris-HCl, pH 7.5, 1 mM EDTA, 1 mM EGTA, 0.5 M Na$_3$VO$_4$, 0.1% (v/v) 2-mercaptoethanol, 1% Triton X-100, 50 mM sodium fluoride, 5 mM sodium pyrophosphate, 10 mM sodium glycerophosphate, 0.1 mM PMSF, 1 µg/mL of aprotinin, pepstatin, leupeptin and 1 µM microcystin). The cleared cell lysates were incubated for 1 hour at 4° C. with 4 µg/tube of anit-Akt1/PKBα PH domain immunoaffinity purified sheep IgG, after which 50 µL of a 1:1 (v/v) protein G-agarose slurry was added for an additional hour of incubation at 4° C. After centrifugation, the immunoprecipitates were washed three times with Buffer A containing 0.5 M NaCl, then two times with Buffer B (50 mM Tris-HCl, pH 7.5, 0.03% (w/v) Brij-35, 0.1 mM EGTA, 0.1% (v/v) 2-mercaptoethanol), and finally twice with 1×Assay Buffer (20 mM MOPS, pH 7.2, 25 mM β-glycerol phosphate, 5 mM EGTA, 1 mM Na$_3$VO$_4$, 1 mM DTT).

The immunoprecipitates were resuspended in 10 µL of ice-cold 1×Assay Buffer, and were sequentially added: 10 µL of 40 µM PKA inhibitor peptide (TYADFIASGRTGRRNAI-NH$_2$—corresponding to residues 7–23 of human PKA inhibitor), 10 µL of Akt/PKB specific substrate peptide (100 µM) (RPRAATF—corresponding to the phosphorylation site of glycogen synthase kinase-3, specifically targeted by Akt/PKB, but not by other protein kinases such as Rsk-2 and p70 S6 kinase), and 10 µL of [$\gamma$-$^{32}$P]ATP stock solution (1×Assay Buffer with 500 µM ATP, 75 mM MgCl$_2$, containing 1 µCi/µL [$\gamma^{32}$-P] ATP, 3000 Ci/mmol). The reaction was incubated at 37° C. for 30 minutes, after which 40 µL of the supernatant was mixed with 20 µL of 40% TCA and incubated for 5 minutes at room temperature. 40 µL of each final fraction were spotted onto the center of a 2 cm×2 cm P81 phosphocellulose paper. The assay squares were washed three times with 0.75% phosphoric acid for five minutes at room temperature, then once with acetone. The squares were then transferred to vials containing a liquid scintillation cocktail and read in a scintillation counter. Blank reaction for the detection of the unspecific background were performed by substituting the cell lysate with Buffer A at the beginning of the procedure, and aspecific endogenous phosphorylation of proteins in the sample extract was estimated by substituting in some samples 1×Assay Buffer for the Akt/PKB specific substrate peptide.

G. Transcriptional Assays

Those skilled in the art are well familiar with methods for conducting transcriptional assays, and such methods are herein incorporated by reference.

Example 2

Involvement of PI3-kinase in Estrogen-induced eNOS Activity

To determine whether PI3-kinase is involved in the activation of eNOS by estrogens, cultured human endothelial cells were treated with $E_2$ in the presence or absence of the PI3-kinase inhibitor, wortmannin. Wortmannin irreversibly inhibits both the lipid kinase and the serine kinase activity of PI3-kinase through covalent interaction with the p110 catalytic subunit 36, and is a selective PI3-kinase inhibitor when used in the low nanomolar range. The eNOS activity was determined using the conversion of L-arginine to L-citrulline. In a concentration-dependent manner, $E_2$ (10 pM-1 $\mu$M, 30 min) increased eNOS activity with maximum effect occurring at an $E_2$ concentration of 1–10 nM and an $EC_{50}$ value of ~0.1 nM (FIG. 1A). The increase in eNOS activity by $E_2$ was completely inhibited by wortmannin (30 nM).

In a time-dependent manner, $E_2$ (10 nM) produced a biphasic increase in eNOS activity with a 2-fold increase occurring acutely within 10 min and a 3- to 4-fold increase occurring after 15 min (FIG. 1B). Interestingly, co-treatment with wortmannin (30 nM) had little or no effect on the initial increase in eNOS activity (i.e. <5 min), but had a greater inhibitory effect on eNOS activity at later timepoints (i.e. 5–10 min). At timepoints of 15 min and later, co-treatment with wortmannin completely inhibited $E_2$-stimulated eNOS activity. Since wortmannin inhibits PI3-kinase activity, these findings suggest that estrogen-induced PI3-kinase activity mediates increase in eNOS activity in a time-delayed manner. Furthermore, these results indicate that the initial increase in $E_2$-stimulated eNOS activity (i.e. <5 min) occurs by mechanisms which are independent of PI3-kinase activation.

Similarly, $E_2$-stimulated eNOS activity and NO production were completely blocked in the presence of a pure estrogen receptor antagonist, ICI 187,780 (10 $\mu$M) (FIGS. 2A and 2B), suggesting that the effect of $E_2$ on eNOS activity was mediated via estrogen receptors. Furthermore, the involvement of estrogen receptors as well as the specificity of $E_2$ action is suggested by the inability of the inactive $E_2$ stereoisomer, 17$\alpha$-estradiol ($\alpha E_2$), to stimulate eNOS activity or NO production. As a control, insulin (100 nM, 30 minutes), a known activator of the PI3-kinase/Akt pathway, was also able to stimulate eNOS activity and NO production. The stimulatory effect of insulin on eNOS activity was also completely blocked in the presence of wortmannin (30 nM). However, acetylcholine-induced (1 $\mu$M, 30 minutes) NO accumulation which occurs via phospholipase C activation was not affected by either wortmannin or the ICI compound. Furthermore, neither wortmannin nor ICI 187,780 alone affected basal eNOS activity.

Example 3

Effect of Tyrosine Kinase and Mitogen-activated Protein (MAP) Kinase Inhibitors on Estrogen-induced eNOS Activation Recent studies suggest the involvement of protein tyrosine kinases and/or MAP kinases in the acute activation of eNOS by $E_2$.[17] Since the time course following $E_2$ stimulation showed a biphasic pattern in eNOS activity with the initial phase of eNOS activation not sensitive to inhibition by wortmannin, this initial phase was investigated to establish if it is mediated by protein tyrosine kinases and/or MAP kinases. Compared to $E_2$ stimulation, co-treatment with the tyrosine kinase inhibitor, genistein (50 $\mu$M), or the MAP kinase kinase (MEK) inhibitor, PD98059 (5 $\mu$M), significantly blocked the initial phase of $E_2$-stimulated eNOS activity (i.e. $\leq$10 min), but had little or no inhibitory effect on the later and more substantial phase of eNOS activation (i.e. $\geq$15 min). In contrast, co-treatment with wortmannin had little or no effect on $E_2$-stimulated eNOS activity during the initial phase of activation (i.e. $\leq$10 min) but completely inhibited the later and more substantial phase of eNOS activation (i.e. $\geq$5 min).

These findings suggest that the tyrosine/MAP kinases mediate the early or acute increase in eNOS activity by estrogens while the relatively later and more substantial increase in eNOS activation is mediated by PI3-kinase. To validate the functionality of the MEK inhibitor, PD98059, at the concentration used in this study, the ability of PD98059 to inhibit $E_2$-induced ERK-1 and -2 phosphorylation was examined. In a time-dependent manner, co-treatment with PD98059 inhibited $E_2$-stimulated ERK-1 and -2 phosphorylation.

Example 4

Role of Non-nuclear Membrane-bound Estrogen Receptors

Since most of the effects of estrogens have been ascribed to mechanisms occurring at the nuclear level, the effect of a transcription inhibitor, actinomycin D (5 $\mu$M, 2 h), on estrogen-induced eNOS activity was investigated (FIG. 4A). Treatment with actinomycin D had no effect on basal or $E_2$-stimulated eNOS activity. Furthermore, actinomycin D had no inhibitory effect on insulin-induced eNOS activity. These findings suggest that $E_2$- and insulin-induced PI3-kinase and eNOS activity occur via non-transcriptional mechanisms. Although $E_2$ and insulin both activate PI3-kinase, they do so with different kinetics. It was discovered that $E_2$-stimulated eNOS activity occurs in a biphasic manner with the later and more substantial phase (i.e. $\geq$15 min) being wortmannin-sensitive (i.e. through PI3-kinase) (FIG. 4B). In contrast, insulin rapidly activates PI3-kinase (data not shown) and eNOS activity within 2 min following stimulation. These findings suggest that the two hormones activate PI3-kinase through different mechanisms.

Example 5

Activation of PI3-kinase by 17$\beta$-estradiol

To determine whether treatment with E2 activates PI3-kinase, PI3-kinase activity was measured using a phosphatidylinositol phosphorylation assay. Treatment with $E_2$ (10 nM) stimulated PI3-kinase activity in a time-delayed manner (FIGS. 5A and 5B). There was little or no PI3-kinase activity following the initial phase of $E_2$ stimulation (i.e. $\leq$10 min). However, at a later timepoint after $E_2$ stimulation (i.e. 20 min), PI3-kinase activity was increased by approximately 5-fold compared to baseline values. These findings are in temporal agreement with the relatively delayed increase in $E_2$-stimulated eNOS activity (FIG. 1B).

The activation of PI3-kinase by $E_2$ was also completely inhibited by ICI 187,780 (10 $\mu$M) and wortmannin (30 nM)

(FIGS. 5A and 5B), suggesting the involvement of estrogen receptor(s) with PI3-kinase. The specificity of $E_2$ action is confirmed by the lack of $\alpha E_2$-stimulated PI3-kinase activity. Stimulation with insulin (100 nM), however, produced a comparable increase in PI3-kinase activity which was completely inhibited by wortmannin (30 nM).

Example 6

Association of Estrogen Receptor (ER)-α with PI3-kinase

To determine whether the estrogen receptor (ER)-a is physically associated with the regulatory subunit of PI3-kinase, p85, co-immunoprecipitation studies were performed with an agarose-conjugated antibody which specifically recognizes ER-α. Subsequent immunoblotting of the immunoprecipitate with an antibody directed against p85 demonstrated that under basal culture conditions, ER-α physically interacts with the p85 subunit of PI3-kinase (FIGS. 6A and 6B). Stimulation with 17β-, but not 17α-, estradiol increased the association of p85 with ER-α by more than 2-fold. This increase in p85/ER-α association by $E_2$ was completely blocked in the presence of the ER-α antagonist, ICI 187,780.

To confirm the specificity of the co-immunoprecipitated p85 band, the PI3-kinase activity was measured in the immunoprecipitate which was pulled down by the ER-α antibody. Under basal culture conditions, there was a small amount of PI3-kinase activity associated with the ER-a (FIGS. 6A and 6B). Stimulation with $E_2$ produced a 2-fold increase in ER-α-associated PI3-kinase activity which was completely blocked in the presence of ICI 187,780. The inactive estrogen isomer, 17α-estradiol ($\alpha E_2$) did not significantly increase ER-α-associated PI3-kinase activity compared to baseline. It is believed that this is the first report showing that the estrogen receptor (i.e. ER-α) directly interacts with the regulatory subunit of PI3-kinase.

Example 7

Activation of Akt/PKB by 17β-estradiol

Since one of the prominent downstream targets of PI3-kinase is the phosphorylation and activation of Akt serine/threonine kinase by PDK-1 and -2,[30, 31] it was investigated whether phosphorylation and activation of Akt is temporally associated with PI3-kinase and eNOS activation by $E_2$. Akt is activated by two independent phosphorylations on the serine 473 (Ser 473)[29] and on threonine 308 (Thr 308) residues.[28] Using an antibody which specifically recognizes the threonine phosphorylation form of Akt, it was found that under basal culture conditions, there is little or no Akt threonine phosphorylation (FIG. 7A). Stimulation with $E_2$ caused an increase in Akt phosphorylation in a time-delayed manner similar to what were observed earlier with PI3-kinase and eNOS activity. The threonine phosphorylation of Akt did not occur until after 20 after stimulation with $E_2$. Furthermore, $E_2$-induced Akt phosphorylation was completely inhibited by wortmannin (30 nM) and to a lesser degree by ICI 187,780. Similarly, insulin-induced Akt threonine phosphorylation was completely inhibited by wortmannin. Interestingly, the 17α-estradiol produced minimal increase in Akt phosphorylation. To determine whether the threonine phosphorylation of Akt correlated with increase in Akt activity, Akt kinase assays were performed on endothelial cells stimulated with $E_2$ in the presence or absence of ICI 187,780 and wortmannin. Stimulation with $E_2$ minimally increased Akt kinase activity by 1.5-fold after 10 min (FIG. 7B). However, after 20 min, E2 stimulation produced a 2.3-fold increase in Akt kinase activity. Co-treatment with ICI 187,780 almost completely inhibited E2-stimulated Akt kinase activity; whereas, wortmannin decreased Akt kinase activity to substantially below basal values. These findings suggest that under basal culture conditions, there is constitutive Akt kinase activity which is mediated by constitutive PI3-kinase activity. The 17a-estradiol produced a small increase in PI3-kinase activity while insulin caused a substantial increase in Akt kinase activity which was completely blocked to below baseline with wortmannin. Thus, the temporal association of PI3-kinase, Akt kinase, and eNOS activity in response to $E_2$ suggest that the PI3-kinase/Akt pathway mediates $E_2$-induced eNOS activity.

Example 8

Interaction of Estrogen Receptor with the Regulatory Subunit of Phosphatidylinositol 3-Kinase Estrogen produces diverse biological effects through binding to the estrogen receptor (ER)[1]. The ER is a steroid hormone nuclear receptor which when bound to estrogen, modulates the transcriptional activity of target genes[2]. Controversy exists, however, as to whether ER has a non-nuclear role[3], particularly in mediating the cardiovascular protective effects of estrogen[4]. Here we show that the ER isoform, ERα, binds in a ligand-dependent manner to the p85α regulatory subunit of phosphatidylinositol 3-kinase (PI3K). Stimulation with estrogen increases ERα-associated PI3K activity leading to the activation of protein kinase B (PKB)/Akt and endothelial nitric oxide synthase (eNOS). The recruitment and activation of PI3K by liganded-ERα are independent of gene transcription; do not involve phosphotyrosine adapter molecules or src-homology (SH) domains of p85α; and extend to other steroid hormone receptors. Mice treated with estrogen showed increased eNOS activity and decreased vascular leukocyte accumulation following ischemia and reperfusion injury. This vascular protective effect of estrogen was abolished in the presence of PI3K or eNOS inhibitors. These findings define a physiologically important non-nuclear estrogen-signaling pathway involving the direct interaction of ERα with PI3K.

PI3K mediates the cellular effects of platelet-derived growth factor (PDGF)[5], insulin[6], and vascular endothelial growth factor (VEGF)[7]. The predominant form of PI3K consists of an 85 kD (p85α) adapter/regulatory subunit and a 110 kD (p110) catalytic subunit[8]. PI3K catalyzes the formation of lipid mediators[9,10] which recruit signaling molecules containing PtdIns-3,4,5-$P_3$-binding or pleckstrin homology (PH) domains such as phosphatidylinositol-dependent kinases and protein kinase Akt[11,12]. The activation of Akt through phosphorylation of Thr308/Ser473[13] mediates many of the downstream cellular effects of PI3K, including stimulation of glucose transporter-4 membrane translocation[14], inactivation of glycogen synthase kinase-3[15], and activation of eNOS[16,17] and cell survival pathways[18]. Although estrogen stimulates eNOS activity[19] and promotes cell survival, it is not known whether PI3K mediates these effects of estrogen.

At physiologic concentrations, 17β-estradiol ($E_2$) increased eNOS activity in a biphasic manner ($EC_{50}$ value of 0.1 nM) (FIG. 8, a and b). The initial increase was mediated by mitogen-activated protein (MAP) kinases[19] while the later increase was completely blocked by the PI3K inhibitor, wortmannin. The increase in eNOS activity was also blocked by the ER antagonist, ICI 187,780, and the inactive $E_2$ stereoisomer, 17α-estradiol (α$E_2$), has no effect. In murine fibroblasts transfected with ERα and eNOS cDNAs, $E_2$ produced an 8-fold increase in eNOS activity in wild-type but not p85α-deficient (p85α-/-) fibroblasts[20] (FIGS. 8c and 14). Furthermore, in p85α-/- fibroblasts, co-transfection of p85αcDNA led to a 4-fold increase in $E_2$-stimulated eNOS activity; whereas, in wild-type fibroblasts, co-transfection of a dominant-negative p85α mutant cDNA decreased $E_2$-stimulated eNOS activity by >50%.

In non-transfected human endothelial cells, $E_2$ increased endogenous PtdIns-3,4,5-$P_3$ levels in a time-delayed manner similar to the wortmannin-sensitive phase of eNOS activation (FIG. 9a). In contrast, insulin rapidly increased endogenous PtdIns-3,4,5-$P_3$ levels[6] and eNOS activity[21]. Increases in PtdIns-3,4,5-$P_3$ levels correlated temporally with the ligand-dependent increases in ERα-associated PI3K activity (FIG. 9b); events which were blocked by ICI 187,780 and wortmannin (FIG. 9c). Consistent with a rapid, non-nuclear effect of ER on eNOS activation, $E_2$-stimulated PI3K activity was blocked by another ER antagonist, tamoxifen, but not by the MAP kinase inhibitor, PD 98059, or by the transcriptional inhibitor, actinomycin D (FIG. 9d). Insulin, which utilizes the phosphotyrosine (p-Tyr) adapter molecule, insulin receptor substrate (IRS)-1, to interact with PI3K, increases PI3K activity in the p-Tyr and IRS-1 immunoprecipitate (FIG. 9e), but did not increase or augment $E_2$-associated PI3K activity. In contrast, $E_2$ did not increase p-Tyr- or IRS-1-associated PI3K activity (FIG. 9e). These findings suggest that ERα does not recruit already activated PI3K by insulin and that PI3K activation by ER and IRS-1 occurs via distinct mechanisms. Interestingly, the activation of PI3K extended to other steroid hormone nuclear receptors such as the thyroid hormone and glucocorticoid receptors (FIG. 9f). These interactions may explain some of the previously unrecognized functions of these nuclear hormone receptors.

ERα interacted with p85α in a ligand-dependent manner in both non-transfected endothelial cells (FIG. 10a) and p85α-/- fibroblasts transfected with ERα and p85α cDNAs (FIG. 10b). This ligand-dependent interaction was blocked by ICI 187,780 and was absent in p85α-/- fibroblasts transfected with ERα cDNA alone. The ER isoform, ERβ, which is thought to mediate some of estrogen's cardiovascular effects[4], however, did not interact with p85α or recruit PI3K activity following $E_2$ stimulation (FIG. 13). Surprisingly, the interaction of ERα and p85α also occurred in the absence of adapter molecules or accessory proteins as human recombinant ERα could still interact with GST-p85α fusion protein in a ligand-dependent manner in a cell-free system (FIG. 10c). This interaction, however, does not involve the SH2/SH3 domains of p85α (FIG. 10d) which are known to interact with p-Tyr residues of growth hormone receptors and adapter molecules[22,23]. Heat shock protein 90, which binds and facilitates the function of ER[24] and eNOS[25], inhibited the interaction of ERα and p85α (FIG. 15).

The generation of PtdIns-3,4,5-$P_3$ leads to the recruitment and activation of Akt[11,26]. $E_2$ stimulated Akt kinase activity in a time-delayed manner (FIG. 10e), similar to what was observed with increases in PtdIns-3,4,5-$P_3$ levels and eNOS activity. To address the question whether $E_2$-stimulated eNOS activation is mediated by Akt, we transiently-transfected bovine aortic endothelial cells (BAEC) with adenoviruses containing constitutively-active (myr) and dominant-negative (dn) Akt mutants[27]. Transfection of BAEC with myr-Akt produced a substantial increase in eNOS activity while over-expression of dn-Akt decreased basal eNOS activity below baseline and completely abolished $E_2$-stimulated eNOS activity (FIG. 10f).

To determine the physiological significance of this pathway, we used an established model of ischemia and reperfusion (I/R) injury in the mouse cremaster muscle[28]. I/R leads to leukocyte recruitment to the vascular wall; an event attenuated by NO and exacerbated by eNOS inhibitors such as L-nitroarginine methylester (L-NAME)[29]. I/R reduced median leukocyte rolling velocity by 13.8 μm/s (p<0.003) and induced a 2.2-fold increase in the number of adherent leukocytes (p<0.001) (FIG. 11, a and b). Treatment with $E_2$ increased eNOS activity by 3.2-fold and prevented the subsequent changes in leukocyte accumulation and rolling velocity following I/R. When wortmannin or L-NAME was applied to the cremaster muscle, measurements of leukocyte rolling velocity and accumulation were not different between untreated and $E_2$-treated mice following I/R, although L-NAME decreased eNOS activity below that of untreated mice (FIG. 11, a, b and c). These findings indicate that the NO-induced vascular protective effect of estrogen is predominantly mediated by PI3K.

While the nuclear function of ER is clearly established, previous studies regarding the membrane and cytoplasmic effects of estrogen remain inconclusive[3]. By linking ER to PI3K, a potential critical step in non-nuclear action is suggested. In addition, the potential biological effects of estrogen are considerably broadened since PI3K is known to mediate various cellular functions[18]. Although most of the ER is localized to the nucleus, we find that there is an increased level of membrane and cytoplasmic ER following $E_2$ stimulation (data not shown). Indeed, a recent study suggest that membrane-associated ER is involved in mediating NO release from endothelial cells[30]. Thus, it is likely that PI3K is being recruited and activated by a small subset of liganded, membrane-associated ER. It remains to be determined, however, whether estrogen can also activate PI3K indirectly, and whether PI3K can account for other rapid, non-nuclear effects of estrogen. Further studies characterizing the interaction domains of ERα and p85α should help clarify these issues.

Methods

Cell Cultures

Human and bovine aortic endothelial cells were harvested enzymatically with Type IA collagenase (1 mg/mL). They were cultured and stimulated under serum-starved conditions consisting of phenol red-free Medium 199 (Gibco BRL, Life Technologies, Gaithersburg, Md.) with 0.4% charcoal-stripped fetal calf serum.

Immunoprecipitations

Cells were washed with ice-cold PBS and lysed with the following buffer: Tris-HCl (20 mM, pH 7.4), EDTA (10 mM), NaCl (100 mM), IGEPAL (1%), $Na_3VO_4$ (1 mM), NaF (50 mM), PMSF (0.1 mg/ml), and aprotinin (0.3 mg/ml). The immunoprecipitating antibody (1 μg) was added to equal amounts of cell lysates (0.5–1 mg) in 500 μl of lysis buffer for 1 h at 4° C. with gentle rocking. Afterwards, 40 μl of 1:1 Protein A-agarose was added and the entire mixture was rocked gently for another 1 hr at 4° C. The mixture was then centrifuged at 12,000 g for 5 min at 4° C. The supernatant was removed and the immunoprecipitate was washed 3 times with 500 μl of washing buffer, which differs from the lysis buffer in having a NaCl concentration of 150 mM instead of 100 mM. The proteins in the washed immunoprecipitate is then separated by SDS-polyacrylamide gel electrophoresis and immunoblotted with anti-ERα (Ab-10: Clone TE11.5D11, NeoMarkers, Fremont, Calif., USA) or anti-p85α (Upstate Biotech., Lake Placid, N.Y., USA) antibody. The efficiency of the immunoprecipitation using ERα and p85α is shown in FIG. 12.

GST Fusion Protein-affinity Purification

Human recombinant GST-p85α fusion protein or GST (Sigma, St. Louis, Mo.) bound to glutathione-agarose beads (1 μg protein/20 μL beads) were suspended in 400 μL of E. Coli protein extract solution (10 mg/mL) and incubated with 1 μg human recombinant ERα (Panvera, Madison, Wis.) for 1 h at 4° C. The samples were pelleted, and the beads were washed 5 times with a buffer containing 50 mM potassium phosphate, pH 7.5, 150 mM KCl, 1 mM $MgCl_2$, 10% (v/v) glycerol, 1% (v/v) Triton X-100 plus protease inhibitors. The beads were re-suspended in 50 μL of 2×Laemmli's buffer and boiled for 5 min. Proteins were separated on SDS-polyacrylamide gel electrophoresis.

Model of Vascular Injury 10-week old, 24 g, male C57BL/6 mice (Hilltop; Scottsdale, Pa.) were subcutaneously implanted with 1.5 mg of slow-release $E_2$ tablets (Innovative Research of America; Sarasota, Fla.), 3–5 days before experiments to ensure steady-state serum $E_2$ levels and to avoid any effects of surgery on baseline hemodynamic parameters. Mice implanted with $E_2$ tablets have a serum $E_2$ level of 760±30 pg/ml compared to that of vehicle-treated mice (24±6 pg/ml). Mice were anesthetized and the cremaster muscle was studied under intravital microscopy[28]. Ischemia was induced by applying pressure to supplying arteries just sufficient to stop blood flow for 30 min. In some experiments, wortmannin (100 nM) or L-NAME (0.1 mM) was applied to the cremaster muscle during the ischemic period. The pressure was released for reperfusion, and the same vessels were recorded in each animal before and after I/R. The rolling velocities of 25 leukocytes were measured in each venule; sorted and averaged for each rank to construct cumulative histograms. The velocities of 3,750 leukocytes were measured in 150 venules before and after I/R. The number of firmly adherent leukocytes was measured before and after I/R in the same 200 μm long segments of venules. The following number of venules were studies for leukocyte adhesion: Untreated, 15 venules; $E_2$-treated, 20 venules; $E_2$-treated with wortmannin, 25 venules; $E_2$-treated with L-NAME, 15 venules. Cremaster eNOS activity was measured in 3 untreated, 4 $E_2$-treated, 5 $E_2$-treated with wortmannin, and 4 $E_2$-treated with L-NAME mice.

References for this Example 8 Only

1. Green, S. et al. Human oestrogen receptor cDNA: sequence, expression and homology to v- erb-A. Nature 320, 134–139 (1986).
2. Kumar, V. et al. Functional domains of the human estrogen receptor. Cell 51, 941–951 (1987).
3. Pietras, R. J. & Szego, C. M. Specific binding sites for oestrogen at the outer surfaces of isolated endometrial cells. Nature 265, 69–72 (1977).
4. Gustafsson, J. A. Novel aspects of estrogen action. J Soc Gynecol Investig 7, S8–9 (2000).
5. Escobedo, J. A. et al. cDNA cloning of a novel 85 kd protein that has SH2 domains and regulates binding of PI3-kinase to the PDGF beta-receptor. Cell 65, 75–82 (1991).
6. Ruderman, N. B., Kapeller, R., White, M. F. & Cantley, L. C. Activation of phosphatidylinositol 3-kinase by insulin. Proc Natl Acad Sci U S A 87, 1411–1415 (1990).
7. Papapetropoulos, A., Garcia-Cardena, G., Madri, J. A. & Sessa, W. C. Nitric oxide production contributes to the angiogenic properties of vascular endothelial growth factor in human endothelial cells. J Clin Invest 100, 3131–3139 (1997).
8. Carpenter, C. L. et al. Purification and characterization of phosphoinositide 3-kinase from rat liver. J Biol Chem 265, 19704–19711 (1990).
9. Auger, K. R., Serunian, L. A., Soltoff, S. P., Libby, P. & Cantley, L. C. PDGF-dependent tyrosine phosphorylation stimulates production of novel polyphosphoinositides in intact cells. Cell 57, 167–175 (1989).
10. Rameh, L. E. & Cantley, L. C. The role of phosphoinositide 3-kinase lipid products in cell function. J Biol Chem 274, 8347–8350 (1999).
11. Stephens, L. et al. Protein kinase B kinases that mediate phosphatidylinositol 3,4,5-trisphosphate-dependent activation of protein kinase B. Science 279, 710–714 (1998).
12. Delcommenne, M. et al. Phosphoinositide-3-OH kinase-dependent regulation of glycogen synthase kinase 3 and protein kinase B/AKT by the integrin-linked kinase. Proc Natl Acad Sci U S A 95, 11211–11216 (1998).
13. Alessi, D. R. et al. Mechanism of activation of protein kinase B by insulin and IGF-1. EMBO J 15, 6541–6551 (1996).
14. Kohn, A. D., Summers, S. A., Birnbaum, M. J. & Roth, R. A. Expression of a constitutively active Akt Ser/Thr kinase in 3T3-L1 adipocytes stimulates glucose uptake and glucose transporter 4 translocation. J Biol Chem 271, 31372–31378 (1996).
15. Cross, D. A., Alessi, D. R., Cohen, P., Andjelkovich, M. & Hemmings, B. A. Inhibition of glycogen synthase kinase-3 by insulin mediated by protein kinase B. Nature 378, 785–789 (1995).
16. Dimmeler, S. et al. Activation of nitric oxide synthase in endothelial cells by Akt-dependent phosphorylation. Nature 399, 601–605 (1999).
17. Fulton, D. et al. Regulation of endothelium-derived nitric oxide production by the protein kinase Akt. Nature 399, 597–601 (1999).
18. Franke, T. F., Kaplan, D. R. & Cantley, L. C. PI3K: downstream AKTion blocks apoptosis. Cell 88, 435–437 (1997).
19. Chen, Z. et al. Estrogen receptor alpha mediates the nongenomic activation of endothelial nitric oxide synthase by estrogen. J Clin Invest 103, 401–406 (1999).
20. Fruman, D. A. et al. Impaired B cell development and proliferation in absence of phosphoinositide 3-kinase p85alpha. Science 283, 393–397 (1999).
21. Zeng, G. & Quon, M. J. Insulin-stimulated production of nitric oxide is inhibited by wortmannin. Direct measurement in vascular endothelial cells. J Clin Invest 98, 894–898 (1996).
22. Fantl, W. J. et al. Distinct phosphotyrosines on a growth factor receptor bind to specific molecules that mediate different signaling pathways. Cell 69, 413–423 (1992).
23. Kapeller, R., Toker, A., Cantley, L. C. & Carpenter, C. L. Phosphoinositide 3-kinase binds constitutively to alpha/beta-tubulin and binds to gamma-tubulin in response to insulin. J Biol Chem 270, 25985–25991 (1995).
24. Picard, D. et al Reduced levels of hsp90 compromise steroid receptor action in vivo. Nature 348, 166–168 (1990).
25. Garcia-Cardena, G. et al. Dynamic activation of endothelial nitric oxide synthase by Hsp90. Nature 392, 821–824 (1998).
26. Burgering, B. M. & Coffer, P. J. Protein kinase B (c-Akt) in phosphatidylinositol-3-OH kinase signal transduction. Nature 376, 599–602 (1995).

27. Fujio, Y. & Walsh, K. Akt mediates cytoprotection of endothelial cells by vascular endothelial growth factor in an anchorage-dependent manner. *J Biol Chem* 274, 16349–16354 (1999).
28. Kanwar, S., Smith, C. W. & Kubes, P. An absolute requirement for P-selectin in ischemia/reperfusion-induced leukocyte recruitment in cremaster muscle. *Microcirculation* 5, 281–287 (1998).
29. Kubes, P., Suzuki, M. & Granger, D. N. Nitric oxide: an endogenous modulator of leukocyte adhesion. *Proc Natl Acad Sci U S A* 88, 4651–4655 (1991).
30. Stefano, G. B. et al. Cell-surface estrogen receptors mediate calcium-dependent nitric oxide release in human endothelia. *Circulation* 101, 1594–1597 (2000).

References for the Disclosure, (Aside from Example 8)

1. Nabulsi A A, Folsom A R, White A, Patsch W, Heiss G, Wu K K, Szklo M. Association of hormone-replacement therapy with various cardiovascular risk factors in postmenopausal women. The Atherosclerosis Risk in Communities Study Investigators [see comments]. *N Engl J Med.* 1993;328:1069–1075.
2. The Writing Group for the PEPI Trial. Effects of Estrogen or Estrogen/Progestin Regimens on Heart Disease Risk Factors in Postmenopausal Women. The Postmenopausal Estrogen/Progestin Interventions (PEPI) Trial. *JAMA.* 1995;273:199–208.
3. Grodstein F, Stampfer M, Manson J, Coditz G, Willett W, Rosner B, Speizer F, Hennekens C. Postmenopausal estrogen and progestin use and the risk of cardiovascular disease. *N Engl J Med.* 1996;335:453–461.
4. Grodstein F, Stampfer M J, Colditz G A, Willett W C, Manson J E, Joffe M, Rosner B, Fuchs C, Hankinson S E, Hunter D J, Hennekens C H, Speizer F E. Postmenopausal hormone therapy and mortality [see comments]. *N Engl J Med.* 1997;336:1769–1775.
5. Wahl P, Walden C, Knopp R, Hoover J, Wallace R, Heiss G, Rifkind B. Effect of estrogen/progestin potency on lipid/lipoprotein cholesterol. *N Engl J Med.* 1983;308:862–867.
6. Koh K K, Mincemoyer R, Bui M N, Csako G, Pucino F, Guetta V, Waclawiw M, Cannon R O, 3rd. Effects of hormone-replacement therapy on fibrinolysis in postmenopausal women. *N Engl J Med.* 1997;336:683–690.
7. Williams J K, Adams M R, Herrington D M, Clarkson T B. Short-term administration of estrogen and vascular responses of atherosclerotic coronary arteries [see comments]. *J Am Coll Cardiol.* 1992;20:452–457.
8. Keaney J F, Jr., Shwaery G T, Xu A, Nicolosi R J, Loscalzo J, Foxall T L, Vita J A. 17 beta-estradiol preserves endothelial vasodilator function and limits low-density lipoprotein oxidation in hypercholesterolemic swine. *Circulation.* 1994;89:2251–2259.
9. Gilligan D M, Badar D M, Panza J A, Quyyumi A A, Cannon R O, 3rd. Acute vascular effects of estrogen in postmenopausal women. *Circulation.* 1994;90:786–791.
10. Reis S E, Gloth S T, Blumenthal R S, Resar J R, Zacur H A, Gerstenblith G, Brinker J A. Ethinyl estradiol acutely attenuates abnormal coronary vasomotor responses to acetylcholine in postmenopausal women. *Circulation.* 1994;89:52–60.
11. Gilligan D M, Quyyumi A A, Cannon R O, 3rd. Effects of physiological levels of estrogen on coronary vasomotor function in postmenopausal women. *Circulation.* 1994;89:2545–2551.
12. Collins P, Rosano G M, Sarrel P M, Ulrich L, Adamopoulos S, Beale C M, McNeill J G, Poole-Wilson P A. 17 beta-Estradiol attenuates acetylcholine-induced coronary arterial constriction in women but not men with coronary heart disease [see comments]. *Circulation.* 1995;92:24–30.
13. Rosano G M, Caixeta A M, Chierchia S, Arie S, Lopez-Hidalgo M, Pereira W I, Leonardo F, Webb C M, Pileggi F, Collins P. Short-term anti-ischemic effect of 17beta-estradiol in postmenopausal women with coronary artery disease. *Circulation.* 1997;96:2837–2841.
14. Guetta V, Quyyumi A A, Prasad A, Panza J A, Waclawiw M, Cannon R O, 3rd. The role of nitric oxide in coronary vascular effects of estrogen in postmenopausal women. *Circulation.* 1997;96:2795–2801.
15. Lantin-Hermoso R L, Rosenfeld C R, Yuhanna I S, German Z, Chen Z, Shaul P W. Estrogen acutely stimulates nitric oxide synthase activity in fetal pulmonary artery endothelium. *Am J Physiol.* 1997;273:L119–126.
16. Caulin-Glaser T, Garcia-Cardena G, Sarrel P, Sessa W C, Bender J R. 17 beta-estradiol regulation of human endothelial cell basal nitric oxide release, independent of cytosolic Ca2+ mobilization. *Circ Res.* 1997;81:885–892.
17. Chen Z, Yuhanna I S, Galcheva-Gargova Z, Karas R H, Mendelsohn M E, Shaul P W. Estrogen receptor alpha mediates the nongenomic activation of endothelial nitric oxide synthase by estrogen. *J Clin Invest.* 1999;103:401–406.
18. Michel T, Li G K, Busconi L. Phosphorylation and subcellular translocation of endothelial nitric oxide synthase. *Proc Natl Acad Sci U S A.* 1993;90:6252–6256.
19. Corson M A, James N L, Latta S E, Nerem R M, Berk B C, Harrison D G. Phosphorylation of endothelial nitric oxide synthase in response to fluid shear stress. *Circ Res.* 1996;79:984–991.
20. Dimmeler S, Assmus B, Hermann C, Haendeler J, Zeiher A M. Fluid shear stress stimulates phosphorylation of Akt in human endothelial cells: involvement in suppression of apoptosis. *Circ Res.* 1998;83:334–341.
21. Dimmeler S, Fissthaler B, Fleming I, Assmus B, Hermann C, Zeiher A M. 1998. Shear stress stimulates the protein kinase Akt—involvement in regulation of the endothelial nitric oxide synthase. In *American Heart Association, 71st Scientific Sessions,* vol. 98. Circulation, ed, Nov. 8–11, 1998, Dallas, Tex.
22. Ruderman N B, Kapeller R, White M F, Cantley L C. Activation of phosphatidylinositol 3-kinase by insulin. *Proc Natl Acad Sci U S A.* 1990;87:1411–1415.
23. Zeng G, Quon M J. Insulin-stimulated production of nitric oxide is inhibited by wortmannin. Direct measurement in vascular endothelial cells. *J Clin Invest.* 1996;98:894–898.
24. Carpenter C L, Duckworth B C, Auger K R, Cohen B, Schaffhausen B S, Cantley L C. Purification and characterization of phosphoinositide 3-kinase from rat liver. *J Biol Chem.* 1990;265:19704–19711.
25. Auger K R, Serunian L A, Soltoff S P, Libby P, Cantley L C. PDGF-dependent tyrosine phosphorylation stimulates production of novel polyphosphoinositides in intact cells. *Cell.* 1989;57:167–175.
26. Escobedo J A, Navankasattusas S, Kavanaugh W M, Milfay D, Fried V A, Williams L T. cDNA cloning of a novel 85 kd protein that has SH2 domains and regulates binding of PI3-kinase to the PDGF beta-receptor. *Cell.* 1991;65:75–82.
27. Gerber H P, McMurtrey A, Kowalski J, Yan M, Keyt B A, Dixit V, Ferrara N. Vascular endothelial growth factor regulates endothelial cell survival through the phosphatidylinositol 3'-kinase/Akt signal transduction pathway.

Requirement for Flk-1/KDR activation. *J Biol Chem.* 1998;273:30336–30343.

28. Stephens L, Anderson K, Stokoe D, Erdjument-Bromage H, Painter G F, Holnes A B, Gaffney P R, Reese C B, McCormick F, Tempst P, Coadwell J, Hawkins P T. Protein kinase B kinases that mediate phosphatidylinositol 3,4,5-trisphosphate-dependent activation of protein kinase B [see comments]. *Science.* 1998;279:710–714.

29. Delcommenne M, Tan C, Gray V, Rue L, Woodgett J, Dedhar S. Phosphoinositide-3-OH kinase-dependent regulation of glycogen synthase kinase 3 and protein kinase B/AKT by the integrin-linked kinase. *Proc Natl Acad Sci U S A.* 1998;95:11211–11216.

30. Franke T F, Yang S I, Chan T O, Datta K, Kazlauskas A, Morrison D K, Kaplan D R, Tsichlis P N. The protein kinase encoded by the Akt proto-oncogene is a target of the PDGF-activated phosphatidylinositol 3-kinase. *Cell.* 1995;81:727–736.

31. Burgering B M, Coffer P J. Protein kinase B (c-Akt) in phosphatidylinositol-3-OH kinase signal transduction [see comments]. *Nature.* 1995;376:599–602.

32. Libby P, Ordovas J M, Auger K R, Robbins A H, Birinyi L K, Dinarello C A. Endotoxin and tumor necrosis factor induce interleukin-1 gene expression in adult human vascular endothelial cells. *Am J Pathol.* 1986;124:179–185.

33. Laufs U, Fata V L, Liao J K. Inhibition of 3-hydroxy-3-methylglutaryl (HMG)-CoA reductase blocks hypoxia-mediated down-regulation of endothelial nitric oxide synthase. *J Biol Chem.* 1997;272:31725–31729.

34. Walsh J P, Caldwell K K, Majerus P W. Formation of phosphatidylinositol 3-phosphate by isomerization from phosphatidylinositol 4-phosphate. *Proc Natl Acad Sci U S A.* 1991;88:9184–9187.

35. Wakeling A E, Dukes M, Bowler J. A potent specific pure antiestrogen with clinical potential. *Cancer Res.* 1991;51:3867–3873.

36. Wymann M P, Bulgarelli-Leva G, Zvelebil M J, Pirola L, Vanhaesebroeck B, Waterfield M D, Panayotou G. Wortmannin inactivates phosphoinositide 3-kinase by covalent modification of Lys-802, a residue involved in the phosphate transfer reaction. *Mol Cell Biol.* 1996;16:1722–1733.

37. Wyckoff M H, Yuhanna I S, Pace M C, Mendelsohn M E, Shaul P W. 1998. Plasma membrane-associated estrogen receptors mediate the acute activation of eNOS by estrogen. In *American Heart Association 71st Scientific Sessions,* vol. 98. Circulation, ed, Nov. 9–11, 1998 Dallas, Tex.

38. Kanai F, Ito K, Todaka M, Hayashi H, Kamohara S, Ishii K, Okada T, Hazeki O, Ui M, Ebina Y. Insulin-stimulated GLUT4 translocation is relevant to the phosphorylation of IRS-1 and the activity of PI3-kinase. *Biochem Biophys Res Commun.* 1993;195:762–768.

39. Cross D A, Watt P W, Shaw M, van der Kaay J, Downes C P, Holder J C, Cohen P. Insulin activates protein kinase B, inhibits glycogen synthase kinase-3 and activates glycogen synthase by rapamycin-insensitive pathways in skeletal muscle and adipose tissue. *FEBS Lett.* 1997;406:211–215.

40. Okada T, Kawano Y, Sakakibara T, Hazeki O, Ui M. Essential role of phosphatidylinositol 3-kinase in insulin-induced glucose transport and antilipolysis in rat adipocytes. Studies with a selective inhibitor wortmannin. *J Biol Chem.* 1994;269:3568–3573.

41. Valius M, Kazlauskas A. Phospholipase C-gamma 1 and phosphatidylinositol 3 kinase are the downstream mediators of the PDGF receptor's mitogenic signal. *Cell.* 1993;73:321–334.

42. Yao R, Cooper G M. Requirement for phosphatidylinositol-3 kinase in the prevention of apoptosis by nerve growth factor. *Science.* 1995;267:2003–2006.

43. Kauffmann-Zeh A, Rodriguez-Viciana P, Ulrich E, Gilbert C, Coffer P, Downward J, Evan G. Suppression of c-Myc-induced apoptosis by Ras signalling through PI(3)K and PKB. *Nature.* 1997;385:544–548.

44. Shepherd P R, Withers D J, Siddle K. Phosphoinositide 3-kinase: the key switch mechanism in insulin signalling [published erratum appears in Biochem J Nov. 1, 1998;335(Pt 3):711]. *Biochem J.* 1998;333:471–490.

45. Spyridopoulos I, Sullivan A B, Kearney M, Isner J M, Losordo D W. Estrogen-receptor-mediated inhibition of human endothelial cell apoptosis. Estradiol as a survival factor. *Circulation.* 1997;95:1505–1514.

46. Datta S R, Dudek H, Tao X, Masters S, Fu H, Gotoh Y, Greenberg M E. Akt phosphorylation of BAD couples survival signals to the cell-intrinsic death machinery. *Cell.* 1997;91:231–241.

47. Cardone M H, Rot N, Stennicke H R, Salvesen G S, Franke T F, Stanbridge E, Frisch S, Reed J C. Regulation of cell death protease caspase-9 by phosphorylation. *Science.* 1998;282:1318–1321.

What is claimed is:

1. A method of identifying a compound which modulates the non-transcriptional, non-MAP-kinase induced effects of a steroid hormone, comprising:
   contacting cells expressing a steroid hormone receptor with a steroid hormone, a tyrosine/MAP kinase pathway inhibitor or transcription inhibitor, and with a range of concentrations of a test compound, and
   measuring the effect of each concentration of said test compound on the activity of phosphatidylinositol-3-kinase in said cells to determine whether said test compound modulates the non-transcriptional, non-MAP-kinase induced effects of the steroid hormone.

2. The method according to claim 1 wherein said steroid hormone is estrogen.

3. The method according to claim 2 which comprises contacting cells with estrogen or an estrogen analog in the presence of a range of concentrations of a test compound.

4. The method according to claim 1 wherein said steroid hormone receptor is a thyroid hormone receptor.

5. The method according to claim 1 wherein said steroid hormone receptor is a glucocorticoid receptor.

6. The method according to claim 1 wherein said contacting of cells with the tyrosine/MAP kinase pathway inhibitor or transcription inhibitor occurs prior to said contacting of cells with the steroid hormone and test compound.

* * * * *